(12) United States Patent
Lipowska et al.

(10) Patent No.: US 9,061,077 B2
(45) Date of Patent: Jun. 23, 2015

(54) METHODS OF DETERMINING RENAL FUNCTION USING TECHNETIUM-99M TRICARBONYL-NITRILOTRIACETIC ACID

(75) Inventors: Malgorzata Lipowska, Decatur, GA (US); Andrew T. Taylor, Jr., Atlanta, GA (US); Luigi Marzilli, Baton Rouge, LA (US)

(73) Assignee: Emory University, Atlanta, GA (US)

( * ) Notice: Subject to any disclaimer, the term of this patent is extended or adjusted under 35 U.S.C. 154(b) by 405 days.

(21) Appl. No.: 12/990,144

(22) PCT Filed: May 5, 2009

(86) PCT No.: PCT/US2009/042767
§ 371 (c)(1),
(2), (4) Date: Nov. 19, 2010

(87) PCT Pub. No.: WO2009/137428
PCT Pub. Date: Nov. 12, 2009

(65) Prior Publication Data
US 2011/0064656 A1    Mar. 17, 2011

Related U.S. Application Data

(60) Provisional application No. 61/151,672, filed on Feb. 11, 2009, provisional application No. 61/050,349, filed on May 5, 2008.

(51) Int. Cl.
| | | |
|---|---|---|
| *A61K 49/04* | (2006.01) | |
| *A61K 51/04* | (2006.01) | |
| *A61B 5/00* | (2006.01) | |
| *A61K 49/00* | (2006.01) | |

(52) U.S. Cl.
CPC ......... *A61K 51/0478* (2013.01); *A61K 49/0004* (2013.01)

(58) Field of Classification Search
CPC ..... A61K 49/0004; A61K 51/00; A61B 5/004
USPC .......................... 424/1.11, 1.65, 9.1, 9.3, 9.36
See application file for complete search history.

(56) References Cited

U.S. PATENT DOCUMENTS

| | | | |
|---|---|---|---|
| 4,017,596 A * | 4/1977 | Loberg et al. ................. 424/1.65 |
| 5,955,053 A * | 9/1999 | Marzilli et al. ............... 424/1.11 |
| 5,986,074 A | 11/1999 | Marzilli et al. | |
| 6,926,883 B1 * | 8/2005 | Dyszlewski et al. ......... 424/1.65 |
| 8,147,805 B2 | 4/2012 | Yang et al. | |
| 2004/0185390 A1 | 9/2004 | Vincent et al. | |
| 2006/0078500 A1 | 4/2006 | Neeman et al. | |

OTHER PUBLICATIONS

Malgorzata Lipowska et al. First Evaluation of a 99mTc-Tricarbonyl Complex, 99mTc(CO)3(LAN), as a New Renal Radiopharmaceutical in Humans, The Journal of Nuclear Medicine, vol. 47(6) 1032-1040, 2006.*

Vanbilloen et al., (2000), "Synthesis and biological evaluation of the four isomers of technetium-99m labeled ethylenecysteamine cysteine (99mTc-ECC), the mono-acid derivative of 99mtc-L,L-ethylenedicysteine.", Nuclear Medicine and Biology, 27(2): 207-214.

Volkmann et al., (1994), "Single-kidney 99mTc-mercatoacetyltriglycine extraction and clearance as compared with para-aminohippurate." In: O'Reilly PH, Taylor A, Nally JV, eds. Radionuclides in Nephrourology., Blue Bell, PA: Field & Wood Medical Periodicals, Inc.; 21-26.

Vrana et al., (1984), "Preparation and characterization of technetium-99m labeled chelates for use in nuclear medicine." Radioisotopy, 25:621-639.

Zinger et al., (1993), "Truncation of the cytoplasmic domain of the simian immunodeficiency virus envelope glycoprotein increases env incorporation into particles and fusogenicity and infectivity.", Journal of Virology, 67(5): 2824-2831.

Taylor, A., et al., 2013, 99mTc(CO)3(NTA) and 131-I-OIH: Comparable Plasma Clearances in Patients with Chronic Kidney Disease, J Nucl Med, 54(4):578-84.

Herman, H. J., et al., 1978, Radiation Dose and Labeling of Hippuran, Contro. Nephrol, 11:100-104.

Rattat, D., et al., 2005, Comparison of 'classic' 99mTc-DTPA, 99Tc(CO03-DTPA and 99m-Tc(CO)2-(NO)-DTPA, Tetrahedron 61:9563-9568.

Alberto et al., (2001), "Synthesis and Properties of Boranocarbonate: A Convenient in Situ CO Source for the Aqueous Preparation of [99mTc(OH2)3(CO)3]+. ", Journal of the American Chemical Society, 123(13): 3135-3136.

Eshima et al., (1992), "Technetium-99 (99mTc) mercaptoacetyltriglycine: Update on the new 99mTc renal tubular function agent.", Seminars in Nuclear Medicine, 22(2): 61-73.

Eshima et al., (1997), "Comparison of SEP-PAK and HPLC Radiochemical Purity Testing of the European and U.S. Tc-99m MAF3 Kit Formulations.", J. Nucl. Med., 38: Proceedings of the 44th Annual Meeting, pp. 49P, No. 177.

He et al., (2005), "Re(CO)3 Complexes Synthesized via an Improved Preparation of Aqueous fac-[Re(CO)3(H2O)3]+ as an Aid in Assessing 99mTc Imaging Agents. Structural Characterization and Solution Behavior of Complexes with Thioether-Bearing Amino Acids as Tridentate Ligands.", Inorganic Chemistry, 44(15): 5437-5446.

(Continued)

*Primary Examiner* — Michael G Hartley
*Assistant Examiner* — Jagadishwar Samala
(74) *Attorney, Agent, or Firm* — Emory Patent Group

(57) ABSTRACT

This disclosure relates to the methods of imaging the kidneys and measuring renal function using the renal tracer $^{99m}$Tc(CO)$_3$(NTA) (technetium-99m tricarbonyl-nitrilotriacetic acid). The disclosure encompasses methods of imaging the kidneys and measuring effective renal plasma flow (ERPF) in an animal or human subject using renal scintigraphy, comprising administering to an animal or human subject an amount of a renal tracer, wherein the renal tracer comprises $^{99m}$Tc-(CO)$_3$(NTA). Another aspect of the disclosure are methods of measuring effective renal plasma flow in an animal or human subject, comprising administering to an animal or human subject an amount of a renal tracer, wherein the renal tracer comprises $^{99m}$Tc-(CO)$_3$(NTA), isolating a series of plasma samples from the animal or human subject after administering the renal tracer and quantitatively detecting the amount of the renal tracer in the biological samples.

10 Claims, 5 Drawing Sheets

(56) References Cited

OTHER PUBLICATIONS

Rosen Gallbladder Uptake Simulating Hydronephrosis on Tc-99m MAG3 Scintigraphy Clinical Nuclear Medicine vol. /8, No. 8, pp. 713-714.

Sanchez et al. Gallbladder Activity Appearing 6 Minutes After the Intravenous Injection of Tc99m MAG3 Simulating a Picture of Obstructive Uropathy of the Right Kidney, Clin Nucl Med, 1993, 18:30-34.

Taylor et al. Technetium-99m MAG3 Kit Formulation: Preliminary Results in Normal Volunteers and Patients with Renal Failure, J Nucl Med, 1988, 29:616-622.

Shattuck et al., Evaluation of the Hepatobiliary Excretion of Technetium-99m-MAG3 and Reconstitution Factors Affecting Radiochemical Purity J Nucl Med, 1994, 35:349-355.

Alberto et al., (1998), "A Novel Organometallic Aqua Complex of Technetium for the Labeling of Biomolecules: Synthesis of [99mTc(OH2)3(CO)3]+ from [99mTcO4]—in Aqueous Solution and Its Reaction with a Bifunctional Ligand.", Journal of the American Chemical Society, 120(31): 7987-7988.

Alberto et al., (2001), "Synthesis and Properties of Boranocarbonate: A Convenient in Situ CO Source for the Aqueous Preparation of [99mTc(OH2)3(CO)3]+.", Journal of the American Chemical Society, 123(13): 3135-3136.

Anghileri, L., (1964), "A simplified method for preparing high specific activity 131I-labeled hippuran.", Int J Appl Radiat Isot, 15:95.

Blaufox et al., (1996), "Report of the Radionuclides in Nephrourology Committee on Renal Clearance.", Journal of Nuclear Medicine, 37(11): 1883-1888.

Bormans et al., (1988), "Evaluation of the Diasteromers of Tc-99m-Mercaptoacetylglycyl-D-Alanylglycine (Tc-99m-D-MAGAG) in Primates.", J. Nucl. Med., 29: Proceedings of the 35th Annual Meeting, pp. 909, No. 705.

Bubeck et al., (1990), "Pharmacokinetics of Technetium-99m-MAG3 in Humans.", Journal of Nuclear Medicine, 31 (8): 1285-1293.

Budny et al., (1973), "Nitrilotriacetate (NTA): Human metabolism and its importance in the total safety evaluation program.", Toxicology and Applied Pharmacology, 25(1): 48-53.

Chatterjee et al., (1991), "Functionalization of hydroxy compounds with nitrilotriacetic acid for technetium-99m chelation: Excretory properties of the radiolabelled chelates.", International Journal of Radiation Applications and Instrumentation. Part B. Nuclear Medicine and Biology, 18(3): 263-274.

Cleynhens et al., (1991), "Comparative Evaluation of Gem-Dimethyl Derivatives of Tc-99m MAG3.", J. Nucl. Med., 32: Proceedings of the 38th Annual Meeting, pp. 1016, No. 451.

Eshima et al., (1987), "Animal Evaluation of Technetium-99m Triamide Mercaptide Complexes as Potential Renal Imaging Agents.", Journal of Nuclear Medicine, 28(7): 1180-1186.

Eshima et al., (1992), "Technetium-99m (99mTc) mercaptoacetyltriglycine: Update on the new 99mTc renal tubular function agent.", Seminars in Nuclear Medicine, 22(2): 61-73.

Eshima et al., (1997), "Comparison of SEP-PAK and HPLC Radiochemical Purity Testing of the European and U.S. Tc-99m MAG3 Kit Formulations.", J. Nucl. Med., 38: Proceedings of the 44th Annual Meeting, pp. 49P, No. 177.

Fesler et al., (2004), "Heterogeneity of Cardiorenal Characteristics in Normotensive Subjects.", Hypertension, 43(2): 219-223.

Fox et al., (2004), "Predictors of new-onset kidney disease in a community-based population.", JAMA, 291(7): 844-850.

Gates, G., (1982). "Glomerular filtration rate: estimation from fractional renal accumulation of 99mTc-DTPA (stannous)." American Journal of Roentgenology 138(3): 565-570.

Gellermann et al., (2004), "Frequently relapsing nephrotic syndrome: treatment with mycophenolate mofetil.", Pediatric Nephrology, 19(1): 101-104.

Halkar et al., (2007), "Monitoring Renal Function: A Prospective Study Comparing Camera-Based Technetium-99m Mercaptoacetyltriglycine Clearance and Creatinine Clearance.", Urology, 69(3): 426-430.

Hansen et al., (1994), "Evaluation of Technetium-99m-Triamide-Mercaptide Complexes Designed to Identify Properties Favoring Renal Tubular Transport.", Journal of Nuclear Medicine, 35(7): 1198-1205.

Hansen et al., (1999), "Factors Influencing the pKa of Ligated Amines and the Syn/Anti Isomerization in Cysteine-Based Re(V)O(N2S2) Radiopharmaceutical Analogues As Revealed by a Novel Dominant Tautomer in the Solid State.", Inorganic Chemistry, 38(23): 5351-5358.

Havranek et al., (1994), "Development of new radiopharmaceuticals—technetium aminopolycarboxylate complexes." Pharmazie 49(5): 369-370.

He et al., (2005), "Re(CO)3 Complexes Synthesized via an Improved Preparation of Aqueous fac—[Re(CO)3(H2O)3]+ as an Aid in Assessing 99mTc Imaging Agents. Structural Characterization and Solution Behavior of Complexes with Thioether-Bearing Amino Acids as Tridentate Ligands.", Inorganic Chemistry, 44(15): 5437-5446.

He et al., (2007), "Initial evaluation of new 99mTc(CO)3 renal imaging agents having carboxyl-rich thioether ligands and chemical characterization of Re(CO)3 analogues.", Nuclear Medicine and Biology, 34(6): 709-716.

Hosick et al., (1966), "The Removal and Control of Iodide-131 Contamination in Sodium O-Iodo131 Hippurate.", Journal of Nuclear Medicine, 7(8): 643-646.

Inoue et al., (1999), "Evaluation of Renal Function from 99mTc-MAG3 Renography Without Blood Sampling.", Journal of Nuclear Medicine, 40(5): 793-798.

Jafri et al., (1988), "Technetium-99m MAG3, a Comparison with Iodine-123 and Iodine-131 Orthoiodohippurate, in Patients with Renal Disorders.", Journal of Nuclear Medicine, 29(2): 147-158.

Lipowska et al., (2006), "First Evaluation of a 99mTc-Tricarbonyl Complex, 99mTc(CO)3(LAN), as a New Renal Radiopharmaceutical in Humans.", Journal of Nuclear Medicine, 47(6): 1032-1040.

Lipowska et al., (2009), "99mTc(CO)3-Nitrilotriacetic Acid: A New Renal Radiopharmaceutical Showing Pharmacokinetic Properties in Rats Comparable to Those of 131I-OIH.", Journal of Nuclear Medicine, 50(3): 454-460.

Marti et al., (2005), "Comparative Studies of Substitution Reactions of Rhenium(I) Dicarbonyl-Nitrosyl and Tricarbonyl Complexes in Aqueous Media.", Inorganic Chemistry, 44(17): 6082-6091.

Miller et al., (1989), "Comparative Pharmacokinetics and Renal Imaging of Tc-99m Mercaptosuccinylglycylglycylglycine (Tc-99m MSG3) and Tc-99m Mertiatide (TechneScan MAG3, Tc-99m MAG3) in Dogs.", J. Nucl. Med., 30: Proceedings of the 36th Annual Meeting, pp. 937-938, No. 889.

Murray et al., (2000), "99Tcm-MAG3: Problems with radiochemical purity testing.", Nuclear Medicine Communications, 21(1): 71-75.

O'Reilly et al., (1996), "Consensus on Diuresis Renography for Investigating the Dilated Upper Urinary Tract.", Journal of Nuclear Medicine, 37(11): 1872-1876.

Piepsz et al., (2001), "Guidelines for glomerular filtration rate determination in children.", European Journal of Nuclear Medicine, 28(3): BP31-36.

Rattat et al., (2004), "Comparison of tridentate ligands in competition experiments for their ability to form a [99mTc (CO)3] complex.", Tetrahedron Letters, 45(12): 2531-2534.

Rattat et al., (2004), "[M(CO)2(NO)]2+, a new core in bioorganometallic chemistry: model complexes of [Re(CO)2 (NO)]2+ and [99mTc(CO)2(NO)]2+.", Tetrahedron Letters, 45(21): 4089-4092.

Rehling et al., (1995), "Renal and extrarenal clearance of 99mTc-MAG3: a comparison with 125I-OIH and 51Cr-EDTA in patients representing all levels of glomerular filtration rate.", European Journal of Nuclear Medicine, 22(12): 1379-1384.

Russell et al., (1988), "Quantitation of Renal Function with Technetium-99m MAG3.", Journal of Nuclear Medicine, 29(12): 1931-1933.

(56) References Cited

OTHER PUBLICATIONS

Sapirstein et al., (1955), "Volumes of Distribution and Clearances of Intravenously Injected Creatinine in the Dog.", American Journal of Physiology—Legacy Content, 181(2): 330-336.

Schaap et al., (1988), "99mTc-MAG3: Dynamic studies in patients with renal disease.", European Journal of Nuclear Medicine, 14(1): 28-31.

Schibli et al., (2002), "Current use and future potential of organometallic radiopharmaceuticals.", European Journal of Nuclear Medicine and Molecular Imaging, 29(11): 1529-1542.

Taylor et al., (1986), "Comparison of Iodine-131 OIH and Technetium-99m MAG3 Renal Imaging in Volunteers.", Journal of Nuclear Medicine, 27(6): 795-803.

Taylor et al., (1989), "Clinical comparison of I-131 orthoiodohippurate and the kit formulation of Tc-99m mercaptoacetyltriglycine.", Radiology, 170(3): 721-725.

Taylor et al., (1995), "Measuring Technetium-99m-MAG3 Clearance with an Improved Camera-Based Method.", Journal of Nuclear Medicine, 36(9): 1689-1695.

Taylor et al., (1997), "Comparison of Technetium-99m-LL-EC Isomers in Rats and Humans.", Journal of Nuclear Medicine, 38(5): 821-826.

Taylor et al., (1997), "Multicenter trial validation of a camera-based method to measure Tc-99m mercaptoacetyltriglycine, or Tc-99m MAG3, clearance.", Radiology, 204(1): 47-54.

Taylor et al., (1999), "A Prospective Study to Compare the Reproducibility of Camera Based MAG3 and Creatinine Clearance Measurements.", J. Nucl. Med., 40: Proceedings of the 46th Annual Meeting, pp. 52P (abstract), No. 209.

Taylor et al., (2004), "99mTc-MAEC Complexes: New Renal Radiopharmaceuticals Combining Characteristics of 99mTc-MAG3 and 99mTc-EC.", Journal of Nuclear Medicine, 45(5): 885-891.

Taylor et al., (2010), "99mTc(CO)3(NTA): A 99mTc Renal Tracer with Pharmacokinetic Properties Comparable to Those of 131I-OIH in Healthy Volunteers.", Journal of Nuclear Medicine, 51(3): 391-396.

Taylor et al., (2013), "99mTc(CO)3(NTA) and 131I-OIH: Comparable Plasma Clearances in Patients with Chronic Kidney Disease.", Journal of Nuclear Medicine, 54(4): 578-584.

Torbjornsdotter et al., (2004), "Nondipping and Its Relation to Glomerulopathy and Hyperfiltration in Adolescents With Type 1 Diabetes.", Diabetes Care, 27(2): 510-516.

Vanbilloen et al., (1996), "Complexes of technetium-99m with tetrapeptides containing one alanyl and three glycyl moieties.", European Journal of Nuclear Medicine, 23(1): 40-48.

\* cited by examiner

METHODS OF DETERMINING RENAL FUNCTION USING TECHNETIUM-99M TRICARBONYL-NITRILOTRIACETIC ACID

CROSS-REFERENCE TO RELATED APPLICATIONS

This application claims priority to U.S. Provisional Patent Application Ser. No. 61/050,349, entitled "Methods of Determining Renal Efficiency Using $^{99M}TC(CO)_3(NTA)$" filed on May 5, 2008, and U.S. Provisional Patent Application Ser. No. 61/151,672, entitled "Methods of Determining Renal Efficiency Using $^{99M}TC(CO)_3(NTA)$" filed on Feb. 11, 2009, the entireties of which are hereby incorporated by reference.

STATEMENT REGARDING FEDERALLY SPONSORED RESEARCH OR DEVELOPMENT

This invention was made with government support under Grants NIH R01 DK38842 awarded by National Institutes of Health. The Government has certain rights in the invention.

FIELD OF THE DISCLOSURE

This disclosure relates to the methods of imaging of a kidney and measuring renal function by using the renal tracer technetium-99m tricarbonyl-nitrilotriacetic acid ($^{99m}Tc(CO)_3(NTA)$).

BACKGROUND

Eight million US adults have kidney disease (Fox et al., (2004) JAMA, 291: 844-850). To develop strategies for prevention and treatment of renal diseases, it is essential to study GFR (glomerular filtration rate), ERPF (effective renal plasma flow) and the filtration fraction (GFR/ERPF). These measurements represent important variables in the investigation and understanding of renal pathophysiology, as well as common diseases such as nephrotic syndrome, hypertension, and diabetes. Such studies enhance our understanding of the pathophysiology of chronic renal injury in humans, help elucidate the mechanisms by which chronic injury progresses to end-stage renal disease, and lead to improved strategies for prevention and therapy (Gellermann & Querfeld (2004) Pediatr. Nephrol. 19: 101-104; Fesler et al., (2004) Hypertension 43: 219-223; Torbjornsdotter et al., (2004) Diabetes Care 27: 510-516).

There is a continuing need for novel renal tracers with a capacity to measure effective renal plasma flow comparable to the current gold standard of para-aminohippurate (PAH). Physicians typically assume that $^{131}$I-ortho-iodohippurate is an excellent agent for the non-invasive measurement of ERPF since it is much easier to measure in plasma and urine than PAH, and there is no risk that the tracer quantities of $^{131}$I-OIH will saturate the organic anion transporter and lead to spuriously low measurements of ERPF. A serious problem with $^{131}$I-OIH, however, is that 15-20% of the $^{131}$I-OIH administered to a patient binds to red blood cells, and the $^{131}$I-OIH must leave the red cells before it can become available for renal tubular extraction. Consequently, when one collects a renal vein blood sample to determine the $^{131}$I-OIH extraction fraction, $^{131}$I-OIH leaves the red cells and re-enters the plasma during the period required to separate the plasma from the red cells, thus leading to a spuriously high measurement of the plasma $^{131}$I-OIH concentration (Rehling et al., (1995) Eur. J. Nucl. Med. 22: 1379-1384). Agents with near zero binding to red blood cells are, therefore, preferred. Additionally, $^{131}$I-OIH is also no longer commercially available in the United States.

For imaging purposes, the first-generation renal tracer technetium-99m mercaptoacetyltriglycine ($^{99m}Tc$-MAG3) has now replaced $^{131}$I OIH. For measuring ERPF, however, $^{99m}Tc$-MAG3 is still far from optimal. The clearance of $^{99m}Tc$-MAG3 is only 50-60% that of $^{131}$I-OIH (see, for example, Taylor et al., (1989) Radiology 170: 721-725; Schaap et al., (1988) Eur. J. Nucl. Med. 14: 28-31; Jafri et al., (1988) J. Nucl. Med. 29: 147-158; Russell et al., (1988) J. Nucl. Med. 29: 1931-1933; Bubeck et al., (1990) J. Nucl. Med. 31: 1285-1293; Blaufox et al., (1996) J. Nucl. Med. 37: 1883-1890; O'Reilly et al., (1996) J. Nucl. Med. 37: 1872-1876). Volkman et al., (In Radionuclides in Nephrology; Edited by O'Reilly et al., 1994; pp. 21-26) concluded that $^{99m}Tc$-MAG3 is not suitable for the accurate estimation of the renal plasma flow because there are marked variations of the extraction fraction of $^{99m}Tc$-MAG3 in kidneys although displaying a constant extraction fraction of PAH. For example, $^{99m}Tc$-MAG3 clearances in 12 volunteers one week apart showed that the $^{99m}Tc$-MAG3 clearance had to change by 35% before a clinician would be 95% confident that the measured change represented a real change in renal function.

Several factors may account for the marked variability of $^{99m}Tc$-MAG3 clearances compared to PAH. Fasting rats have almost twice the hepatobiliary clearance of $^{99m}Tc$-MAG3 as rats with free access to food: 11.7% versus 6.6%, respectively. However, variations in hepatic transport with meals are not sufficient to explain the observed variability in $^{99m}Tc$-MAG3 clearance since it has also been shown that only 0.5-1.0% of the injected $^{99m}Tc$-MAG3 is transported into the small intestine via the hepatobiliary system in normal volunteers. This percentage increases in patients with renal failure. Similarly, variations in the radiochemical purity following kit reconstitution are an unlikely explanation since it has been shown that the 95-96% radiochemical purity of the European $^{99m}Tc$-MAG3 kit is comparable to the US kit (Eshima et al., (1997) J. Nucl. Med. 38: 49P; Murray et al., (2000) J. Nucl. Med. Commun. 21: 71-75).

The most likely factor contributing to the clearance variations is a variation in protein binding. Protein binding of $^{99m}Tc$-MAG3 in rats is sensitive to physiological changes. For example, the protein binding of $^{99m}Tc$-MAG3 decreased from 78% to 44% following PAH infusion and decreased to 42%, 63% and 65%, respectively, following mannitol, ammonium chloride and sodium bicarbonate infusion. A decrease in protein binding secondary to drugs, accumulation of organic acids, or a change in the physiological state could increase the $^{99m}Tc$-MAG3 clearance by making a higher fraction of the $^{99m}Tc$-MAG3 available for both glomerular filtration and tubular transport.

Another ERPF$^{99m}Tc$ tracer is $^{99m}Tc$-LL-ethylene dicysteine (Vanbilloen et al., (2000) Nucl. Med. Biol. 27: 207-214; Vanbilloen et al., (1996) Eur. J. Nucl. Med. 23: 40-48; Cleynhens et al., (1991) J. Nucl. Med. 32: 1016; Bormans et al., (1988) J. Nucl. Med. 29: 909; Miller et al., (1989) J. Nucl. Med. 30: 937-938). However, although $^{99m}Tc$-LL-ethylene dicysteine and $^{99m}Tc$-DD-ethylene dicysteine have a higher clearance than $^{99m}Tc$-MAG3 in humans, the clearance of $^{99m}Tc$-DD-ethylene dicysteine, was still only about 60-65% of that of PAH (Taylor et al., (1997) J. Nucl. Med. 38: 821-826). These agents do not provide a reliable means of monitoring renal function because the solution structure of both DD- and LL-ethylene dicysteine exist in carboxyl ligated monoanionic (20%) and deligated dianionic (80%) forms in rapid equilibrium at physiological pH. They differ markedly in structure and charge, have different rates of clearance and different protein binding affinities, and consequently are affected differently by changes in pH, drugs that affect protein binding, and different renal pathologies. For sequential monitoring of renal function, therefore, a radiopharmaceutical to measure ERPF should exist as a single species at physiological pH.

Finally, a tracer may have a high affinity for an organic anion tubular transporter; however, if the tracer's plasma protein binding is high, it may be relatively unavailable to the transporter, leading to a low EF and, consequently, a low clearance (Eshima et al., (2000) J. Nucl. Med. 41: 2077-2082). Bubeck has postulated that the peritubular transit time is too short for complete dissociation of the highly protein-bound tracers such as $^{99m}$Tc-MAG3 and $^{131}$I-OIH (Bubeck et al., (1990) J. Nucl. Med. 31: 1285-1293).

There is, therefore, a continuing need for renal tracers with an improved capacity to measure effective renal plasma flow (ERPF) comparable to the gold standard, para-aminohippurate (PAH).

SUMMARY

This disclosure relates to the methods of imaging of a kidney and measuring renal function using the renal tracer $^{99m}$Tc(CO)$_3$(NTA). To develop a $^{99m}$Tc renal tracer with a capacity to measure effective renal plasma flow (ERPF) comparable to that of the clinical gold standard, $^{131}$I-ortho-iodohippurate ($^{131}$I-OIH), and superior to that of $^{99m}$TcO-mercaptoacetyltriglycine ($^{99m}$TcO-MAG3), which has a clearance only 50-60% that of $^{131}$I-OIH, $^{99m}$Tc tricarbonyl nitrilotriacetic acid (Na$_2$[$^{99m}$Tc(CO)$_3$(NTA)]), was used. This radiopharmaceutical, which is based on an aminopolycarboxylate ligand, is formed as a single species and has a dangling carboxylate group favoring tubular transport.

One aspect of the present disclosure, therefore, encompasses methods of measuring the relative renal plasma flow in an animal or human subject using renal scintigraphy, comprising administering to an animal or human subject an amount of a renal tracer comprising $^{99m}$Tc-(CO)$_3$(NTA), obtaining at least one image, or a series of images, of a kidney of the animal or human subject, where the image is obtained as a data output from a gamma camera, and analyzing the data output to provide a measurement of the percentage of the total effective renal plasma flow distributed to each kidney of the animal or human subject.

In one embodiment of the methods of the disclosure, multiple images of the kidneys may be obtained over a period of about 20-30 minutes after administration of $^{99m}$Tc-(CO)$_3$(NTA) to an animal or human subject. These images are acquired on a computer and, with image processing, parameters can be measured that together describe the rate of uptake and excretion of $^{99m}$Tc-(CO)$_3$(NTA) by the kidney. These parameters may be useful in detecting obstruction of one or both kidneys and of renovascular hypertension resulting from narrowing of the renal artery causing an increase in blood pressure.

In another embodiment of the disclosure, a gamma camera may be used to quantify the amount of the renal tracer $^{99m}$Tc-(CO)$_3$(NTA) extracted by the kidneys of the animal or human subject. This measurement may be used to determine the effective renal plasma flow of the animal or human subject.

Another aspect of the present disclosure provides methods of measuring effective renal plasma flow in an animal or human subject, the methods comprising administering to an animal or human subject an amount of a renal tracer comprising $^{99m}$Tc-(CO)$_3$(NTA), obtaining one or more biological samples from the animal or human subject after administering the renal tracer, determining the amount of the renal tracer in the biological samples, and determining the effective renal plasma flow of the animal or human subject based on the dose injected, the time interval to the biological samples and the amount of $^{99m}$Tc-(CO)$_3$(NTA) in each sample.

Yet another aspect of the disclosure provides kits comprising an amount of $^{99m}$Tc-(CO)$_3$(NTA) in a sealed container, where the amount may be suitable for imaging the kidneys and providing measurements of renal function, and instructions for the use thereof, comprising a method of measuring renal efficiency in an animal or human subject using renal scintigraphy, comprising administering to an animal or human subject an amount of a renal tracer comprising $^{99m}$Tc-(CO)$_3$(NTA), obtaining at least one image of a kidney of the animal or human subject, where the image may be obtained as a data output from a gamma camera, and analyzing the data output such that the data analysis provides a measurement of the renal efficiency of the animal or human subject.

Yet another aspect of the disclosure is a kit comprising an amount of $^{99m}$Tc-(CO)$_3$(NTA) in a sealed container, where the amount is suitable for use in the measurement of renal function, and instructions for the use thereof, where the method of measuring effective renal plasma flow in an animal or human subject, comprises administering to an animal or human subject an amount of a renal tracer, where the renal tracer comprises $^{99m}$Tc-(CO)$_3$(NTA), isolating a series of biological samples from the animal or human subject after administering the renal tracer, quantitatively detecting the amount of the renal tracer in the biological samples, and determining the effective renal plasma flow of the animal or human subject based on the dose injected, the time from the dose injected to the time of collection of the plasma samples and the amount of $^{99m}$Tc-(CO)$_3$(NTA) in each plasma sample.

BRIEF DESCRIPTION OF THE DRAWINGS

Many aspects of the disclosure can be better understood with reference to the following figures. Please see the following figure legends, text and examples for a description of the Figures.

Figure 1:
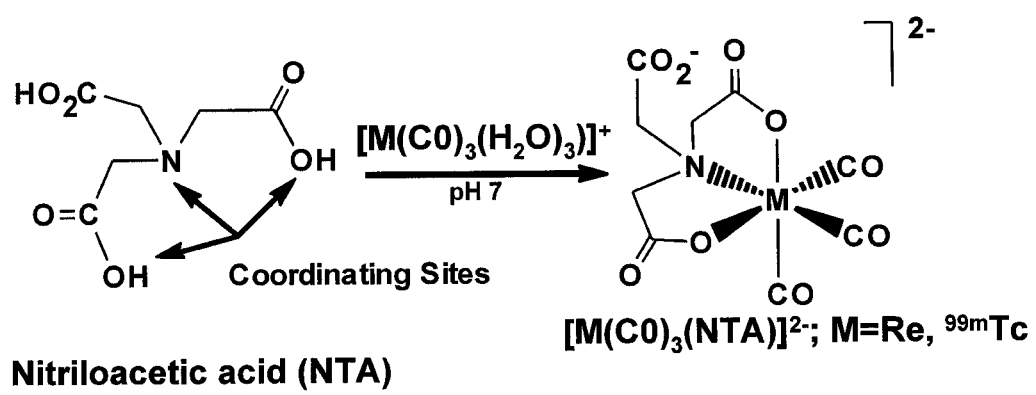
FIG. 1 illustrates a scheme for the synthesis of [M(CO)$_3$(NTA)]$^{2-}$; M=Re (2 h, room temperature) and $^{99m}$Tc (15 min, 70° C.).

The details of some exemplary embodiments of the methods and systems of the present disclosure are set forth in the description below. Other features, objects, and advantages of the disclosure will be apparent to one of skill in the art upon examination of the following description, figures, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations $^{99m}Tc(CO)_3(NTA)$: technetium-99m tricarbonyl-nitrilotriacetic acid; $^{99m}Tc$-MAG3; technetium-99m mercaptoacetyltriglycine; EC: ethylene dicysteine; PAH: para-aminohippurate; OIH: ortho-iodohippurate; GFR: glomerular filtration rate; ERPF: effective renal plasma flow; GFR/ERPF; filtration fraction; MAG: mercaptoacetyltriglycine; NTA: nitrilotriacetic acid; bw: body weight; DTPA: diethylenetriaminepentaacetic acid; OTf: trifluoromethanesulfonate or triflate;

Definitions

Generally the terms and phrases used herein have their art-recognized meaning which can be found by reference to standard texts, journal references and contexts known to those skilled in the art. The following definitions are provided to clarify their specific use in the context of this disclosure.

The term "animal or human subject" as used herein refers to any animal, including, but not limited to, domestic animals such as the dog, cat, rabbits, agricultural animals such as cow, sheep, horse and the like, non-domesticated animals, including those held by a zoo or in the wild and birds, as well as any adult or juvenile human.

The term "renal scintigraphy" as used herein refers to an imaging system including, but not limited to, a gamma camera able to detect and form an image localizing a source of gamma radiation. In the context of the present disclosure, the imaging system may be for an image corresponding to the form of the labeled organ, and in particular of a kidney underlying skin and other tissues. The imaging system may further comprise computer-based apparatus and software intended to produce an image in a form apparent to the observer, and to analyze the image for information such as, but not only, the intensity of the emitted gamma radiation as well as its locality in the subject body.

The term "dose amount" as used herein refers to a bolus dose of a renal tracer, and in particular of the tracer $^{99m}$Tc-(CO)$_3$(NTA). The dose is preferred to be of an amount that, when delivered to the kidney of an animal or human subject, will have a gamma intensity useful for forming an image of the gamma source by a gamma camera. The administered dose may be between about 11.11 MBq [0.3 mCi] to about 370 MBq (about 10 mCi) of $^{99m}$Tc(CO)$_3$(NTA), the dose amount being adjusted according to the size, weight, and shape of the recipient subject and the purpose of the study.

The terms "renal blood flow (RBF)" and "effective renal plasma flow (ERPF)" as used herein refer, in the physiology of the kidney, to the volume of blood delivered to the kidneys per unit time. In humans, the kidneys together receive roughly 20% of cardiac output, amounting to 1 L/min in a 70-kg adult male. RBF is closely related to renal plasma flow (RPF), which is the volume of blood plasma delivered to the kidneys per unit time. While the terms generally apply to arterial blood delivered to the kidneys, both RBF and RPF can be used to quantify the volume of venous blood exiting the kidneys per unit time. In this context, the terms are commonly given subscripts to refer to arterial or venous blood or plasma flow, as in $RBF_a$, $RBF_v$, $RPF_a$, and $RPF_v$. Physiologically, however, the differences in these values are negligible so that arterial flow and venous flow are often assumed equal.

Renal blood flow calculations are based on renal plasma flow and hematocrit (HCT). This follows from the fact that hematocrit estimates the fractional volume of blood occupied by red blood cells. Hence, the fraction of blood that is in the form of plasma is given by 1−HCT and RPF=RBF(1−HCT).

Values of $P_v$ are difficult to obtain in patients. In practice, PAH (para-aminohippurate) clearance may be used instead to calculate the effective renal plasma flow (ERPF). PAH is freely filtered, efficiently extracted by the renal tubular cells and it is not reabsorbed by the kidney so that its venous plasma concentration is usually about 10% of the PAH arterial plasma concentration; consequently. ERPF usually underestimates RPF by approximately 10%.

Discussion

Prerenal azotemia accounts for about 70% of community-acquired cases of acute renal failure and 40% of hospital-acquired cases. Acute renal failure is present in about 1% of patients on admission to the hospital, occurs with a frequency of 2-5% during hospitalization and may occur with a frequency of 4-15% of patients after cardiopulmonary bypass. Prerenal azotemia affects up to 5% of hospitalized patients, and sustained prerenal azotemia is the most common factor that predisposes patients to ischemia-induced tubular necrosis. A tracer that can non-invasively measure ERPF can provide an important clinical parameter to help the clinician distinguish between renal and prerenal azotemia. With prompt diagnosis and appropriate therapy, prerenal azotemia is rapidly reversible and the morbidity and the high costs of acute tubular necrosis can be prevented.

Measurement of the filtration fraction in patients requires an accurate non-invasive measurement for approximating renal plasma flow. PAH can be used to estimate renal plasma flow, but the assay is cumbersome. $^{99m}$Tc-(CO)$_3$(NTA) of the present disclosure provides an agent advantageous for the measurement of ERPF compared to the commercially available agent $^{99m}$Tc-MAG3.

Serial monitoring of renal function can be critically important in managing the patient whose renal function might be changing, such as a renal transplant patient, a patient taking nephrotoxic drugs, a diabetic patient, and a patient with renal, heart, and liver failure. While the serum creatinine is often used as a measure of renal function, it is a very insensitive indicator; a person can lose more than 50% of renal function and the serum creatinine may still remain in the normal range. Moreover, the creatinine clearance is a notoriously unreliable method of following renal function. Even with the inherent limitations of $^{99m}$Tc-MAG3, it has been shown that camera-based $^{99m}$Tc-MAG3 clearance is a more reproducible measurement of renal function than is the creatinine clearance (Taylor et al., (1999) J. Nucl. Med. 40: 52P (abstract); Halkar et al., (2007) Urology 69: 426-430). Plasma sample clearances require substantial technical expertise, conformity with CLIA (Clinical Laboratory Improvement Act) and are not practical in the typical radiology department in the United States.

Maximum diagnostic and clinical management utility is not being realized from current nuclear scans. Camera-based clearances using tubular agents require only 4 minutes of imaging time (Schlegel & Hamway (1976) J. Urol. 116: 2882-2885; Gates, (1982) Am. J. Radiol. 138: 565-570; Taylor et al., (1995) J. Nucl. Med. 36: 1689-1695; Taylor et al., (1997) Radiology 204: 47-54; and Inoue at al., (1999) J. Nucl. Med. 40: 793-798) and have an inherently greater accuracy and precision than camera-based clearances using a GFR agent such as $^{99m}$Tc-DTPA.

Accordingly, a tracer with a clearance approaching that of PAH would expand the potential for camera-based clearances because the extraction fraction (EF) will approach 90%, which is, much higher than the 20% EF of $^{99m}$Tc-DTPA and the 50-60% EF of $^{99m}$Tc-MAG3. The higher kidney to background ratios minimize errors associated with background correction and would allow more reliable renal function measurements to become a routine component of the estimated 440,000 imaging studies performed annually in the United States. For many patients, it is not critical to have a precise measure of renal function, but it is extremely important to know if renal function is improving, deteriorating or remaining stable. Camera-based clearances using the $^{99m}$Tc-(CO)$_3$(NTA) tracer of the present disclosure, with a clearance approaching that of PAH, provides a simple and reliable answer to this common clinical problem.

The improved diagnostic accuracy provided by $^{99m}$Tc-MAG3 compared to $^{99m}$Tc-DTPA is due to the clearance in humans of $^{99m}$Tc-MAG3 being about 2-2.5 times the clearance of $^{99m}$Tc-DTPA. This superiority is most apparent in patients with impaired renal function, particularly those with suspected obstruction (O'Reilly et al., (1996) J. Nucl. Med. 37: 1872-1876; and Gordon at al (2001) Eur. J. Nucl. Med. 28: BP31-36)

It is in the same adult and pediatric patient population, particularly those with impaired function and/or possible obstruction, that the imaging advantages of a second generation tubular agent with a clearance of about 1.5-2.0 higher than that of $^{99m}$Tc-MAG3 itself are likely to be most apparent. The $^{99m}$Tc tubular agents of the present disclosure have a more rapid clearance and urinary excretion with lower patient radiation dose compared to $^{99m}$Tc-DTPA and $^{99m}$Tc-MAG3. Although the reduction in radiation dose may be modest, many physicians prefer to keep the radiation dose (particularly to children) as small as possible, and even a small reduction in radiation exposure may be significant.

$^{99m}$Tc complexes of nitrilotriacetic acid and nitrilotriacetic acid derivatives have previously been prepared by stannous reduction of pertechnetate and investigated in rats (Chatterjee et al., (1991) Nucl Med Biol. 18: 263-274; Havranek at al., (1994) Pharmazie 49: 369-370), and in dogs (Vrana & Kleisner (1984) Radioisotopy 25: 621-639). These results, however, have been disappointing with regard to the rate and specificity for renal excretion. The stannous reduction labeling procedure likely produced a mixture of products, including dimers, trimers and tetramers, all with very different rates and specificities for renal excretion. Consequently, the suboptimal renal characteristics of $^{99m}$Tc-NTA prepared by stannous reduction may not be applicable to a well-characterized tracer with a tricarbonyl core, such as Na$_2$[$^{99m}$Tc(CO)$_3$(NTA)].

Na$_2$[$^{99m}$Tc(CO)$_3$(NTA)] of the present disclosure is highly hydrophilic, with a dangling carboxylate group favoring tubular transport rather than hepatobiliary excretion, and it is formed as a single species with a well-established structure based on the analytical characterization of its Re analogue. The Re(I) center and the anionic part of the [NTA]$^{2-}$ ligand (as shown in FIG. 1), the tertiary amine and both carboxylate groups from the coordinated IDA chelating moiety, have a net negative charge. At pH 7.4, the pendant carboxyl group is deprotonated (the pK$_a$ of the carboxylic acid is approximately 3); thus, both the Re and $^{99m}$Tc complexes have a dianionic overall charge at physiological pH, similar to Na$_2$[$^{99m}$TcO(MAG3)], Na$_2$[$^{99m}$TcO(EC)], Na$_2$[$^{99m}$TcO(MAEC)], and Na$_2$[$^{99m}$Tc(CO)$_3$(CMSA)] (CMSA=carboxymethylmercaptosuccinic acid).

Na$_2$[$^{99m}$Tc(CO)$_3$(NTA)] encompassed by the present disclosure, and as described in the Examples below, was prepared by using commercially available NTA as a trisodium salt monohydrate (NTA) and an IsoLink kit, and isolated by HPLC. Its stability in isotonic saline was assessed for 24 hours, and was further evaluated by incubation in 0.1 M cysteine and histidine for 4 hours at 37° C. The biodistribution of Na$_2$[$^{99m}$Tc(CO)$_3$(NTA)], coinjected with $^{131}$I-OIH as an internal control, was evaluated in 5 normal Sprague-Dawley rats at 10 and 60 mins (Group A) and in 6 rats with renal pedicle ligation at 60 mins (Group B) post-injection. Clearance and extraction fraction studies were conducted in two normal Sprague-Dawley rats, and urine and plasma from two additional normal rats each were analyzed for metabolites by HPLC.

The radiochemical purity of Na$_2$[$^{99m}$Tc(CO)$_3$(NTA)] was >99%, the complex was stable for 24 h at physiological pH, and the challenge experiments showed no degradation. In normal rats, the percent dose in the urine at 10 and 60 mins was 108±9% and 101±5%, respectively, that of $^{131}$I-OIH; there was minimal hepatic/gastrointestinal activity. In Group B rats, Na$_2$[$^{99m}$Tc(CO)$_3$(NTA)] was better retained in the blood and had less excretion into the bowel than $^{131}$I-OIH (P<0.01). The plasma clearances of Na$_2$[$^{99m}$Tc(CO)$_3$(NTA)] and $^{131}$I-OIH were comparable, but the extraction fraction of Na$_2$[$^{99m}$Tc(CO)$_3$(NTA) was 93.5±3.8% compared to 67.9±6.1% for $^{131}$I-OIH. Plasma protein binding of Na$_2$[$^{99m}$Tc(CO)$_3$(NTA) averaged 67±7% and red cell uptake was 7±2%. Na$_2$[$^{99m}$Tc(CO)$_3$(NTA)], therefore, is stable, exists as a single species, and has pharmacodynamic properties in rats comparable to those of $^{131}$I-OIH.

Na$_2$[$^{99m}$Tc(CO)$_3$(NTA)] of the present disclosure is a stable complex, and its pharmacokinetic characteristics in normal rats were advantageous over those of the other $^{99m}$Tc-tricarbonyl renal tubular tracers, and comparable to those of $^{131}$I-OIH, as shown in Table 2. In humans, a renal tracer must be highly specific for renal excretion so that its plasma clearance provides an accurate measurement of renal function; consequently, the tracer should not be cleared via the hepatobiliary tract or secreted across the intestinal mucosa in patients with impaired renal function.

In the animal model of renal failure, Na$_2$[$^{99m}$Tc(CO)$_3$(NTA)] had significantly less intestinal activity than $^{131}$I-OIH. In addition, the renal clearance of Na$_2$[$^{99m}$Tc(CO)$_3$(NTA)] in rats was comparable to that of $^{131}$I-OIH, which was equivalent to that reported in the literature (Eshima et al., (1987) J. Nucl. Med. 28: 1180-1186). Although Na$_2$[$^{99m}$Tc(CO)$_3$(NTA)] and $^{131}$I-OIH had similar clearances, the extraction fraction (EF) of Na$_2$[$^{99m}$Tc(CO)$_3$(NTA)] appeared to be higher than that of $^{131}$I-OIH (93.5% versus 67.9%). This observation may reflect an underestimation of the $^{131}$I-OIH extraction fraction because of dissociation or leakage of $^{131}$I-OIH from the red blood cells back into the plasma in the renal vein sample prior to or during centrifugation. The data as shown in the Examples of the present disclosure, support that the red cell uptake of $^{131}$I-OIH in rats was 35%, compared to 7% for Na$_2$[$^{99m}$Tc(CO)$_3$(NTA)]; consequently, leakage of the tracer from the red cells back into the renal vein plasma would be more problematic for $^{131}$I-OIH than for Na$_2$[$^{99m}$Tc(CO)$_3$(NTA)]. The minimal red cell binding is another advantage of Na$_2$[$^{99m}$Tc(CO)$_3$(NTA)] compared to $^{131}$I-OIH because, under equilibrium conditions, 15-20% of the activity is from $^{131}$I-OIH in human blood bound to or inside of the red cells (Eshima & Taylor (1992) Semin. Nucl. Med. 22: 61-73).

The kinetics and metabolism of the NTA ligand alone have been investigated in several species, including humans (Budny & Arnold (1973) Toxicol. Appl. Pharmacol. 25: 48-53; Health Canada, (1990) Environmental and Workplace Health. Nitrilotriacetic acid (NTA); World Health Organization. (1996) Nitrilotriacetic acid in drinking-water. Guidelines for drinking-water quality. Health criteria and other supporting information. Vol 2. 2nd ed; Geneva). NTA has not been found to be teratogenic or genotoxic but has induced urinary tract tumors in rats and mice at extremely high doses, of about 840 mg/kg bw per day for two years (National Cancer Institute. (1977) NCI-CG-TR-6; DHEW Publication No. [NIH] 77-806). The oral LD$_{50}$ of Na$_3$NTA.H$_2$O in rodents is about 2000 mg/kg bw (Anderson et al., (1985) CRC Critical Reviews of Toxicology 15: 1-102).

Limited information exists regarding the toxicity of NTA in humans. Eight human volunteers did ingest a single dose of 10 mg of NTA, and physical examination, blood chemistry analysis, and urinalysis showed no evidence of adverse effects (Budny & Arnold (1973) Toxicol. Appl. Pharmacol. 25: 48-53). Because NTA induces tumors only at doses higher than those that are nephrotoxic, NTA is classified in Group IIIB (possibly carcinogenic to man). On the basis of two-year studies in rats to determine the lowest no-observed-adverse-effect level for a nephrotoxic effect, Health Canada has determined the acceptable daily intake in drinking water to be 10 μg/kg bw per day (Health Canada, (1990) Environmental and Workplace Health. Nitrilotriacetic acid (NTA).

No free NTA ligand was injected because the ligand was separated from the complex by HPLC prior to injection, and even the administered dose of the Na$_2$[$^{99m}$Tc(CO)$_3$(NTA)] complex was extremely small (less than 0.2 μg/kg bw), which is lower than the acceptable daily intake of NTA; consequently, even if all the $^{99m}$Tc dissociated from the complex, the remaining NTA would still be a safe level. In a kit formulation, free NTA may be injected, but when on the same order as MAG3 (1 mg/vial) then the dose of NTA injected (μg/kg bw) would still be below the toxicity level established by Health Canada for acceptable daily intake.

Studies in normal rats showed that Na$_2$[$^{99m}$Tc(CO)$_3$(NTA)] is excreted in the urine as rapidly as $^{131}$I-OIH, has a high specificity for renal excretion, has minimal activity associated with red cells and has lower activity than $^{131}$I-OIH in the liver at 60 mins (P<0.05). In the renal failure model (renal pedicle ligation), Na$_2$[$^{99m}$Tc(CO)$_3$(NTA)] showed higher retention than $^{131}$I-OIH in the blood at 60 mins and less activity in the bowel, suggesting that in these respects it may be superior to $^{131}$I-OIH in humans. Moreover, Na$_2$[$^{99m}$Tc(CO)$_3$(NTA)] is formed as a single species and is amenable to kit formulation; furthermore, the unreacted NTA is below accepted toxicity levels in humans. These data suggest that the Na$_2$[$^{99m}$Tc(CO)$_3$(NTA)] tracer of the present disclosure is an acceptable $^{99m}$Tc renal tubular imaging agent for imaging and for the measurement of effective renal plasma flow in man.

The present disclosure, therefore, encompasses the use of the renal tracer $^{99m}$Tc-(CO)$_3$(NTA) in methods of imaging the kidney, and measuring ERPF of an animal or human subject. In particular, the $^{99m}$Tc-(CO)$_3$(NTA) can replace the use of $^{99m}$Tc-MAG3 for renal scintigraphy and in camera-based assays of renal function. In the methods of the present disclosure, the tracer $^{99m}$Tc-(CO)$_3$(NTA) may be administered to a recipient animal or human subject and images of the gamma emissions by the tracer in the kidneys are periodically taken using a gamma camera. In general diagnostic use, it is contemplated that a series of images may be taken over a period of between about 2 mins and 60 mins, more advantageously between about 3 mins and 30 mins. The image data from the camera may be further analyzed by suitable software such as, but not limited to, QUANTEM™ or QUANTEM™-II. QUANTEM™-II is a particularly useful application for processing renal studies for research purposes, and is based on the commercial QuantEM methodology, designed by Taylor et al., (1995) J. Nucl. Med. 36: 1689-1695), and developed for use with the radiopharmaceutical Tc-$^{99m}$ MAG3. QuantEM has been previously validated in a multicenter trial ((1997) Radiology. 204: 47-54).

It is also contemplated that, besides images over the renal area, static images may also be taken of the pre-injection dose syringe, post-imaging empty dose syringe, the pre-voided bladder, the post-void-bladder, the post-void kidneys, and the injection site. The syringe images are necessary for calculation of renal clearance by the camera-based method. Bladder images are necessary in order to obtain urine flow rate and residual urine volume. The post-void kidney image is a visual indicator of the emptying of urine from the renal collecting systems (since the patient will usually have gotten up from the scan table in order to void). This image also provides kidney counts, from whole kidney regions of interest, which allow calculation of important ratios relevant to the excretory function of the kidneys. The injection site image is a quality control element for the radiopharmaceutical injection, since a significant quantity of the dose outside the vein will invalidate the study.

The baseline study may be analyzed quantitatively and the results reviewed by a physician. If the patient was referred for evaluation of possible obstruction, adequate clearance of the radiopharmaceutical should be seen and, if it is not, an intravenous dose of furosemide, a diuretic, can be administered. An additional dynamic image set is then acquired. The principles of using this method to quantify renal function are more fully detailed, for example, in Taylor et al., Radiology (1997) 204; 47-54, incorporated herein by reference in its entirety.

One aspect of the present disclosure, therefore provides methods of imaging a kidney in an animal or human subject, the method comprising: (a) administering to an animal or human subject an amount of a renal tracer, where the renal tracer comprises technetium-99m tricarbonyl-nitrilotriacetic acid ($^{99m}$Tc-(CO)$_3$(NTA)); (b) detecting $^{99m}$Tc-(CO)$_3$(NTA) in the kidney of the animal or human subject with a gamma camera; and (c) obtaining at least one image of the kidney of the animal or human subject, where the image is obtained as a data output from a gamma camera.

Another aspect of the present disclosure encompasses methods of measuring renal function in an animal or human subject using renal scintigraphy, comprising: (a) administering to an animal or human subject an amount of a renal tracer, where the renal tracer comprises $^{99m}$Tc-(CO)$_3$(NTA); (b) obtaining at least one image of a kidney of the animal or human subject, wherein the image is obtained as a data output from a gamma camera; and (c) analyzing the data output from the gamma camera, wherein the data analysis provides a measurement of the effective renal plasma flow of the animal or human subject In embodiments of the disclosure, the methods may further comprise repeating the steps (a)-(c), thereby providing a time-dependent analysis of the urinary tract function of an animal or human subject, wherein the analysis is selected from the group consisting of: the EPRF of a kidney, the ability of a kidney to extract the tracer from the blood, the ability of subject human or animal to excrete the tracer into the collecting system of a kidney, monitoring of drainage of the tracer from the collecting system (calyces and pelvis) to the bladder, and to quantify the ability of the bladder to empty.

In other embodiments of the disclosure, the methods may further comprise repeating the steps (a)-(c) at least once, thereby providing a series of images and a time-dependent analysis of renal efficiency of the animal or human subject.

In another embodiment of the disclosure, the methods may further comprise repeating the steps (b) and (c) after a single amount of the renal tracer $^{99m}$Tc-(CO)$_3$(NTA), obtaining a series of images of the kidney or kidneys of the animal or human subject, and analyzing the data output from the gamma camera, wherein the data analysis provides a measurement of the effective renal plasma flow of the animal or human subject.

In one embodiment of this aspect of the disclosure, the steps (a)-(c) may be repeated at time intervals over a period of about 2 mins to 60 mins, thereby providing a time-dependent series of images.

In another embodiment, the steps (a)-(c) are repeated at time intervals over a period of about 3 mins to 30 mins, thereby providing a time-dependent series of images.

Yet another aspect of the disclosure are method of measuring effective renal plasma flow in an animal or human subject, comprising administering to an animal or human subject an amount of a renal tracer, wherein the renal tracer comprises $^{99m}$Tc-(CO)$_3$(NTA), isolating a series of biological samples from the animal or human subject after administering the renal tracer, quantitatively detecting the amount of the renal tracer in the biological samples, and determining the effective renal plasma flow of the animal or human subject.

Another aspect of the present disclosure provides kits comprising: an amount of $^{99m}$Tc-(CO)$_3$(NTA) in a sealed container, wherein the amount is suitable for imaging a kidney of an animal or human subject, and instructions for the use thereof in imaging said kidney and optionally for determining renal function in the animal or human subject.

In one embodiment of this aspect of the disclosure, the instructions comprise the steps of: administering to an animal or human subject an amount of a renal tracer, where the renal tracer comprises technetium-99m tricarbonyl-nitrilotriacetic acid ($^{99m}$Tc-(CO)$_3$(NTA)); detecting $^{99m}$Tc-(CO)$_3$(NTA) in the kidney of the animal or human subject with a gamma camera; and obtaining at least one image of the kidney of the animal or human subject, wherein the image is obtained as a data output from a gamma camera.

In another embodiment of this aspect of the disclosure, the instructions comprise steps for the use of the tracer in measuring renal function, the instructions comprising the steps of: administering to an animal or human subject an amount of a renal tracer, where the renal tracer comprises $^{99m}$Tc-(CO)$_3$(NTA); obtaining at least one image of a kidney of the animal or human subject, wherein the image is obtained as a data output from a gamma camera; and analyzing the data output from the gamma camera, wherein the data analysis provides a measurement of the effective renal plasma flow of the animal or human subject.

In yet another embodiment of the kits of the present disclosure, the instructions for the use of the tracer in measuring renal function compris the steps of: administering to an animal or human subject an amount of a renal tracer, where the renal tracer comprises $^{99m}$Tc-(CO)$_3$(NTA); isolating a plurality of biological samples from the animal or human subject after administering the renal tracer; quantitatively measuring the amount of the renal tracer in the isolated biological samples; and determining the effective renal plasma flow of the animal or human subject.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight and temperature is in ° Celsius.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

EXAMPLES

Example 1

Nitrilotriacetic acid, was purchased from Aldrich. [Re(CO)$_3$ (H$_2$O)$_3$]OTf was prepared as previously reported (He et al., (2005) Inorg. Chem. 44: 5437-5446, incorporated herein by reference in its entirety) and was stored and used as a 0.1 M stock aqueous solution. $^1$H NMR spectra were recorded on a Varian 600-MHz spectrometer in D$_2$O. Electrospray mass spectrometry (ESI-MS) was performed on a Thermo Finnigan LTQ-FT instrument. $^{99m}$Tc-pertechnetate ($^{99m}$TcO$_4^-$) was eluted from a $^{99}$Mo/$^{99m}$Tc generator (Amersham Health) with 0.9% saline. ISOLINK™ vials were obtained from Covidien, Inc, MO. Analysis of the radiolabeled and non-radiolabeled compounds was performed on an HPLC instrument (Beckman System Gold Nouveau) equipped with a Model 170 radiometric detector and a Model 166 ultraviolet light-visible light detector, 32 Karat chromatography software, and a Beckman C18 RP Ultrasphere octyldecyl silane column (5-µm, 4.6×250 mm). Tissue/organ radioactivity was measured with a gamma counter [Packard Cobra II Gamma Counter (Perkin Elmer)].

Example 2

Synthesis of Na$_2$[Re(CO)$_3$(NTA)

The synthesis of the [Re(CO)$_3$(NTA)]$^{2-}$ complex has been previously reported (Marti et al., (2005) lnorg. Chem. 44: 6082-6091, incorporated herein by reference in its entirety); however, that method used (NEt$_4$)$_2$[Re(CO)$_3$Br$_3$] as a Re tricarbonyl precursor and required heating at 80° C. for 2.5 h to form the Na/NEt$_4$[Re(CO)$_3$(NTA)] complex in good yield, but as a mixture of Na/NEt$_4$ salts. To avoid byproducts containing the [NEt$_4$]$^+$ counterion, and to obviate an extensive purification process, [Re(CO)$_3$(H$_2$O)$_3$]OTf precursor was used and gave Na$_2$[Re(CO)$_3$(NTA)] complex exclusively as a Na$^+$ salt, as confirmed by MS, in 89% yield after only 2 h of stirring at room temperature.

Accordingly, the Na$_2$[Re(CO)$_3$(NTA)] complex was synthesized as a nonradioactive reference compound. A solution of nitrilotriacetic acid (NTA) (0.082 g, 0.3 mmol in 3 mL of water) was added to a 0.1 M aqueous solution of [Re(CO)$_3$(H$_2$O)$_3$]OTf (3 mL); the pH was adjusted to 7 with 1 M NaOH, and the reaction mixture was stirred at room temperature for 2 hours. The volume of the reaction mixture was reduced to 2 mL by rotary evaporation, and this solution was passed through a Sephadex G-15 column (eluted with deionized water). The product fractions were collected, the solvent was removed under vacuum, and the white residue was dried to yield Na$_2$[Re(CO)$_3$(NTA)] (0.134 g, 89%). $^1$H NMR [δ (ppm)]: 4.07 (s, 2H), 4.04 (d, 2H, J=16.8 Hz), 3.9 (d, 2H, J=16.8 Hz)]. MS (ESI): m/z 506 (100%, M+Na$_2$)$^+$; HRMS calcd. C$_9$H$_7$O$_9$NNa$_2$$^{187}$Re 505.94684, found 505.94691. Both $^1$H NMR and MS confirmed the identity of the purified product. The only signals present in the $^1$H NMR spectrum were those from the coordinated NTA ligand, consistent with data reported in the literature (Marti et al., 2005 Inorg. Chem. 44: 6082-6091).

Example 3

Radiosynthesis of Na$_2$[$^{99m}$Tc(CO)$_3$(NTA)]

The NTA ligand was labeled as previously described (Rattat et al., (2004) Tetrahedron Lett. 45: 2531-2534, incorporated herein by reference in its entirety). Briefly, 0.5 mL of a freshly prepared solution of the [$^{99m}$Tc(CO)$_3$(H$_2$O)$_3$]$^+$ precursor (pH about 7-8) was added to a vial containing approximately 1.0 mg of the NTA ligand in 0.2 mL of water. The pH of the solution was adjusted to about 7 with 1 M NaOH, heated at 70° C. for 15 mins and cooled to room temperature. Na$_2$[$^{99m}$Tc(CO)$_3$(NTA)] was separated from unlabeled ligand by HPLC; the radiochemical purity was >99%. Methanol was partially removed by $N_2$ gas, and the aqueous solution of $Na_2[^{99m}Tc(CO)_3(NTA)]$ was buffered in a physiological phosphate buffer at pH 7.4.

The NTA ligand was successfully labeled with the $^{99m}Tc$-tricarbonyl precursor, as shown in FIG. 1, and $Na_2[^{99m}Tc(CO)_3(NTA)]$ was isolated with the high radiochemical purity of more than 99%. Because Tc and Re complexes with identical ligands have essentially identical coordination parameters, we confirmed the identity of $Na_2[^{99m}Tc(CO)_3(NTA)]$ by coinjecting it with $Na_2[Re(CO)_3(NTA)]$ and comparing their HPLC profiles. The Re and $^{99m}Tc$-tricarbonyl complexes had the same retention time (17 min).

Example 4

Radiosynthesis of $^{131}I$-OIH $^{131}I$-OIH was prepared by the isotope exchange reaction between non-radioactive hippuran (OIH) and radioactive sodium iodide ($Na^{131}I$) according to the method reported by Anghileri (1964) in Int. J. Appl. Radiat. Isotopes. 15: 95, incorporated herein by reference in its entirety, with modifications as follows: Cold OIH (10-20 mg) and ammonium sulfate (5-10 mg) were placed in a sterile vial, which was closed with a rubber stopper and sealed with aluminum. $Na^{131}I$ (1 mL of 185-370 MBq/mL solution) was transferred to the vial and a syringe filled with activated carbon was connected to the vial via a needle placed through the rubber stopper. The solution was heated at 140° C. for 30 min. During the heating, all the solvent evaporated, leaving solid residue at the bottom of the vial. Sterile water (1 mL) was added to the dry residue and the process was repeated. After cooling to room temperature, the solid residue was dissolved in 5 mL of saline; the solution was then transferred to a vial containing microporous carbon chips which had been impregnated with freshly precipitated silver chloride (Rattat et al., (2004) Tetrahedron Lett.; 45: 2531-2534, incorporated herein by reference in its entirety, and the vial was shaken for 10 min. Next the solution was passed through a sterile Millex-GS 0.22 μm filter unit into a sterile, pyrogen-free empty vial to ensure sterility. The final concentration was approximately 111-296 MBq/5 mL.

The radiochemical purity of $^{131}I$-OIH was determined by thin-layer chromatography (TLC) using silica gel plates (Merck 60F-254) as the solid phase and ethanol:ethyl acetate: ammonium hydroxide (20:20:1) as a mobile phase. In this system the $^{131}I$-OIH had a retention factor (Rf) of 0.3, and radioiodide had a Rf of 0.9. $^{131}I$-OIH was obtained with a 98-99% labeling yield.

Example 5

In Vitro and In Vivo Stability of $Na_2[^{99m}Tc(CO)_3(NTA)]$

The stability of $Na_2[^{99m}Tc(CO)_3(NTA)]$ was examined in vitro in a physiological phosphate buffer at pH 7.4. The buffered solution was evaluated by HPLC at 24 h to assess stability. HPLC analysis of an aliquot of the incubated sample revealed only intact $^{99m}Tc$ complex for 24 h. In addition, HPLC-purified samples of $Na_2[^{99m}Tc(CO)_3(NTA)]$ (0.1 mL) were mixed with 0.1 M solutions of histidine and cysteine (0.9 mL) and incubated at 37° C.; aliquots were analyzed by HPLC at 1, 2 and 4 h to evaluate decomposition. When challenged with an excess of cysteine and histidine at 37° C. for 4 h, $Na_2[^{99m}Tc(CO)_3(NTA)]$ was completely inert and showed no sign of transchelation or decomposition.

Figure 2A:
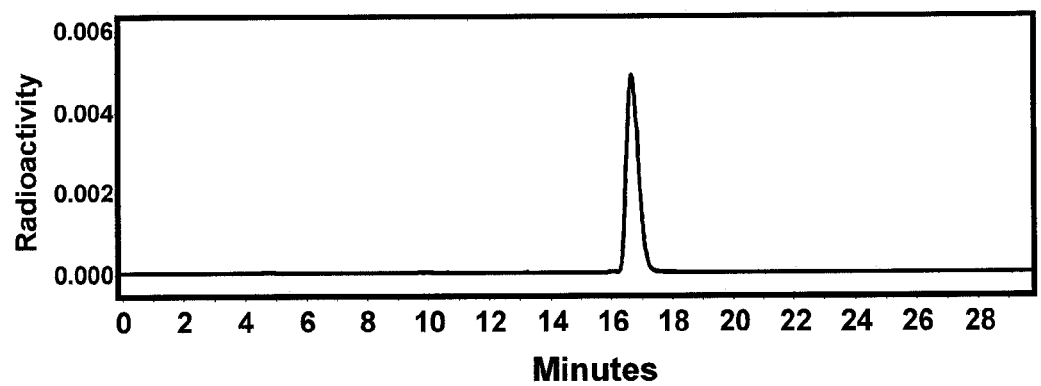
FIGS. 2A-2C illustrate a series of HPLC chromatograms of [$^{99m}$Tc(CO)$_3$(NTA)]$^{2-}$ before injection (FIG. 2A), in the urine at 10 mins post-injection (FIG. 2B), and in the plasma at 2-3 mins post-injection (FIG. 2C).
Figure 2B:
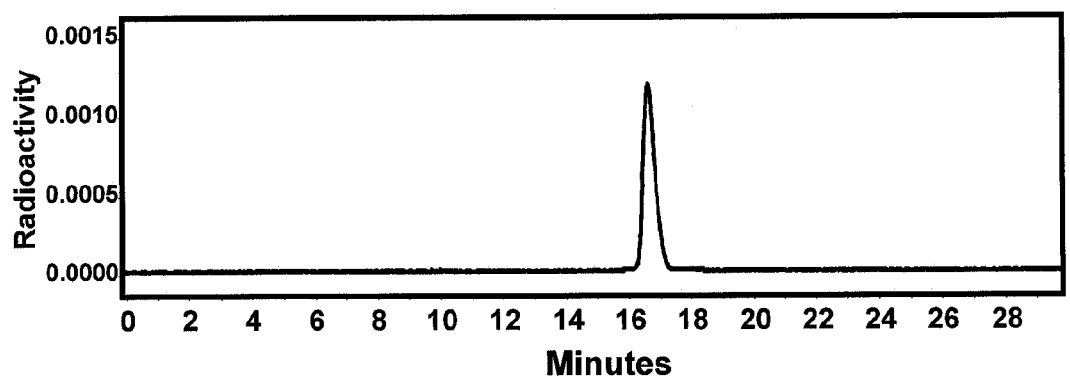
Figure 2C:
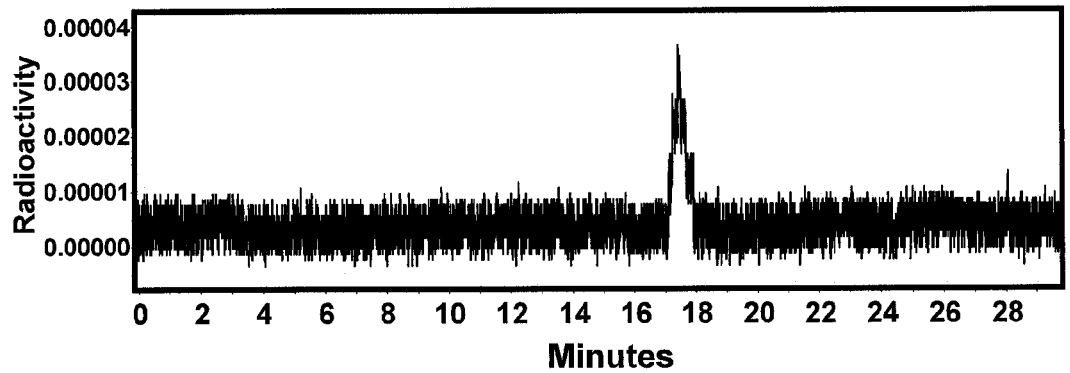

To assess in vivo stability, four rats were anesthetized and injected with 18.5 Mbq [0.5 mCi] of $Na_2[^{99m}Tc(CO)_3(NTA)]$ via a tail vein. Two rats were prepared for a 10-minute urine collection as described above and arterial blood was collected from the remaining two rats at 2-3 mins post-injection by cardiac puncture. Urine and plasma samples were analyzed by HPLC to determine if the complex was metabolized in the plasma or by the kidney. As shown in FIGS. 2A-2C, there was only one peak in urine (FIG. 2B) and plasma (FIG. 2C), and each had an elution time identical to that of the injected complex (FIG. 2A), indicating in vivo stability.

Example 6

Animal Studies $^{99m}Tc(CO)_3(NTA)$ was evaluated in two groups of Sprague-Dawley rats at 10 mins (n=5) and 60 mins (n=6), respectively. For each study group, solutions of $^{99m}Tc$-labeled complex (3.7 MBq/ml [100 μCi/ml]) and $^{131}I$-OIH (925 kBq/ml [25 μCi/ml]) was prepared separately (the pH of that solution was checked to be 7.4), and 0.2-ml samples were drawn into insulin syringes. Five samples for the 10 mins study, and six samples for the 60 mins study were used; the one sample for each time point was diluted to 100 ml, and three 1-ml portions of the resulting solution were used as standards. Each rat was anesthetized with ketamine-xylazine (2 mg/kg of body weight) injected intramuscularly, with additional supplemental anesthetic as needed. The bladder was catheterized by use of heat-flared PE-50 tubing (Becton, Dickinson and Co.) for urine collection.

The radiopharmaceutical solution of $^{99m}Tc(CO)_3(NTA)]$ was injected intravenously via a tail vein; 5 animals were sacrificed at 10 mins after injection, and 6 animals were sacrificed at 60 mins after injection. A blood sample was obtained, and the heart, lungs, spleen, liver, intestines, stomach, and kidneys were removed. The whole liver was weighed, and random sections were obtained for counting. Blood, urine, whole organs, and tissue samples were placed in tubes, and each sample was weighed. The radioactivity of the sample and standards was measured by use of a dual-channel well counter with 20% windows centered on the photo peaks of $^{99m}Tc$ (140 keV) and $^{131}I$ (363 keV). Counts were corrected for background radiation, physical decay, and spillover of $^{131}I$ counts into the $^{99m}Tc$ window. The percentage of the dose in each tissue or organ was calculated by dividing the counts in each tissue or organ by the total injected counts, using reference counts from an accurately diluted sample of the original injection. The value given for the bowel represented combined stomach and intestine activities. The percentage injected dose in whole blood was estimated by assuming a blood volume of 6.5% of total body weight.

$^{99m}Tc(CO)_3(NTA)$ was excreted in the urine of rats at the same rate as $^{131}I$-OIH with minimal uptake in other organs, as shown in Table 1. Comparison with published data for the rate of excretion (percent of the injected dose in the urine at 10 and 60 minutes) for other $^{99m}Tc$-containing agents (Table 2) shows that $^{99m}Tc(CO)_3(NTA)$ is comparable to $^{99m}Tc$-MAG3 and superior to other $^{99m}Tc$ agents.

TABLE 1

Percentage of injected dose in rats of $^{99m}Tc(CO)_3(NTA)$ compared with $^{131}I$-OIH in blood, urine and selected organs

| | 10 min $^{99m}Tc(CO)_3$ (NTA) (%) | 10 min $^{131}I$-OIH (%) | 60 min $^{99m}Tc(CO)_3$ (NTA) (%) | 60 min $^{131}I$-OIH (%) |
|---|---|---|---|---|
| Blood | 4.2 ± 0.9 | 5.6 ± 1.0 | 0.4 ± 0.2 | 0.5 ± 0.0 |
| Kidney | 6.1 ± 0.7 | 5.6 ± 0.6 | 0.4 ± 0.2 | 0.5 ± 0.0 |
| Urine | 57.1 ± 8.4 | 53.2 ± 7.2 | 93.0 ± 4.0 | 91.4 ± 3.7 |
| Urine ($^{99m}Tc/^{131}I$) | 108 ± 9 | | 101 ± 5 | |
| Liver | 2.7 ± 1.2 | 4.0 ± 0.7 | 0.3 ± 0.2 | 0.7 ± 0.2 |
| Bowel | 0.8 ± 0.3 | 2.5 ± 0.5 | 0.4 ± 0.1 | 1.7 ± 0.7 |
| Heart | 0.1 ± 0.1 | 0.2 ± 0.1 | 0.0 ± 0.0 | 0.0 ± 0.0 |
| Lung | 0.4 ± 0.2 | 0.5 ± 0.2 | 0.1 ± 0.1 | 0.1 ± 0.1 |

(at 10 mins (n = 5); 60 mins (n = 6))

TABLE 2

The injected doses in urine in rats at 10 and 60 mins (as a percentage of $^{131}I$-OIH) of $^{99m}Tc(CO)_3(NTA)$, $^{99m}Tc(CO)_3(CMSA)^a$, $^{99m}Tc(CO)_3(TDSA)]^a$, $^{99m}Tc(CO)_3(LAN)^b$, $^{99m}Tc(CO)_3(ENDAC)^c$ and $^{99m}TcO(MAG_3)^{d,e}$.

| Urine ($^{99m}Tc/^{131}I$ ratio) | $^{99m}Tc(CO)_3$ (NTA) | $^{99m}Tc(CO)_3$ $(CMSA)^a$ | $^{99m}Tc(CO)_3$ $(TDSA)^a$ | $^{99m}Tc(CO)_3$ $(LAN)^b$ | $^{99m}Tc(CO)_3$ $(ENDAC)^c$ | $^{99m}TcO$ $(MAG_3)^{d,e}$ |
|---|---|---|---|---|---|---|
| 10 min | 108 ± 9 | 82 ± 4 | 41 ± 5 | 69 ± 6 | 56 ± 5 | 107 ± 0.3 |
| 60 min | 101 ± 5 | 98 ± 1 | 68 ± 8 | 89 ± 6 | 90 ± 4 | 103 ± 0.5$^d$ |

$^a$He et al., (2007) Nucl. Med. Biol. 34: 709-716
$^b$Lipowska et al., (2006) J. Nucl. Med. 47: 1032-1040
$^c$Lipowska et al., (2001) J. Nucl. Med. 42: 259P.
$^d$Eshima ert al., (1987) J. Nucl. Med. 28: 1180-1186
$^e$Biodistribution of $[^{99m}TcO(MAG_3)]^{2-}$ was evaluated in mice (n = 5) at 10 mins at 120 mins post-injection.
Data are mean ± SD.

A solution containing $Na_2[^{99m}Tc(CO)_3(NTA)]$ (3.7 MBq/mL [100 µCi/mL]) and $^{131}I$-OIH (925 kBq/mL [25 µCi/mL]) was prepared (pH about 7.4) and 0.2-mL doses were injected intravenously via a tail vein. One additional aliquot (0.2 mL) for each time point was diluted to 100 mL, and three 1-mL portions of the resulting solution were used as standards.

In Group A, 5 animals were sacrificed at 10 min, and 5 animals were sacrificed at 60 mins after injection. A blood sample was obtained, and the kidneys, heart, lungs, spleen, whole stomach and sections of the duodenum and ascending colon were removed and placed in counting vials. The whole liver was weighed, and random sections were obtained for counting. Samples of blood and urine were also placed in counting vials and weighed. Each sample and the standards were placed in a gamma-counter; counts were corrected for background radiation, physical decay, and spillover of $^{131}I$ counts into the $^{99m}Tc$ window. The percentage of the dose in each tissue or organ was calculated by dividing the counts in each tissue or organ by the total injected counts. The percentage injected dose reported for the bowel was based on the combined counts of the duodenum and colon samples. The percentage injected dose in whole blood was estimated by assuming a blood volume of 6.5% of total body weight.

The 6 Group B rats were sacrificed 60 mins after injection. Selected organs, blood, and all of the small and large intestines were collected and counted as described above. The percentage injected dose reported for the bowel was based on the combined counts in the small and large intestines.

Figure 3A:
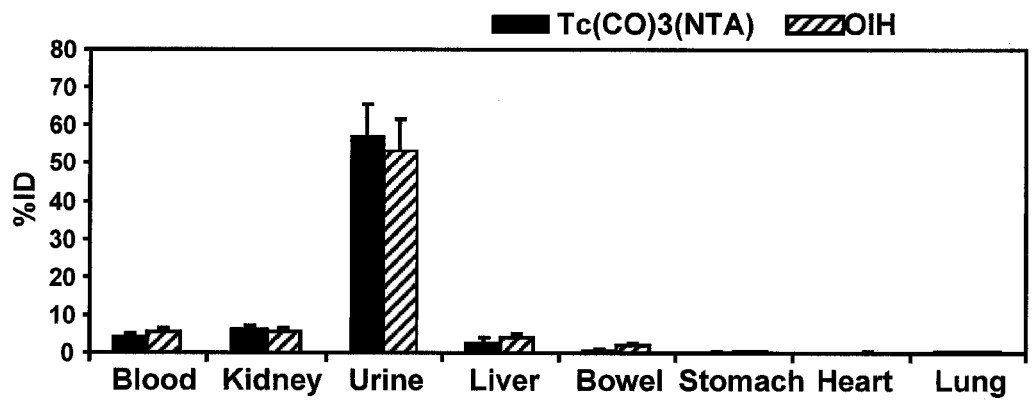
FIGS. 3A-3C illustrate a series of graphs showing the biodistribution of [$^{99m}$Tc(CO)$_3$(NTA)]$^{2-}$ and $^{131}$I-OIH in normal rats (n=5) at 10 mins post-injection (FIG. 3A) and 60 mins post-injection (FIG. 3B) and in rats with renal pedicle ligation (n=6) at 60 mins post-injection (FIG. 3C), expressed as a percentage of the injected dose (% ID)/organ, blood and urine.
Figure 3B:
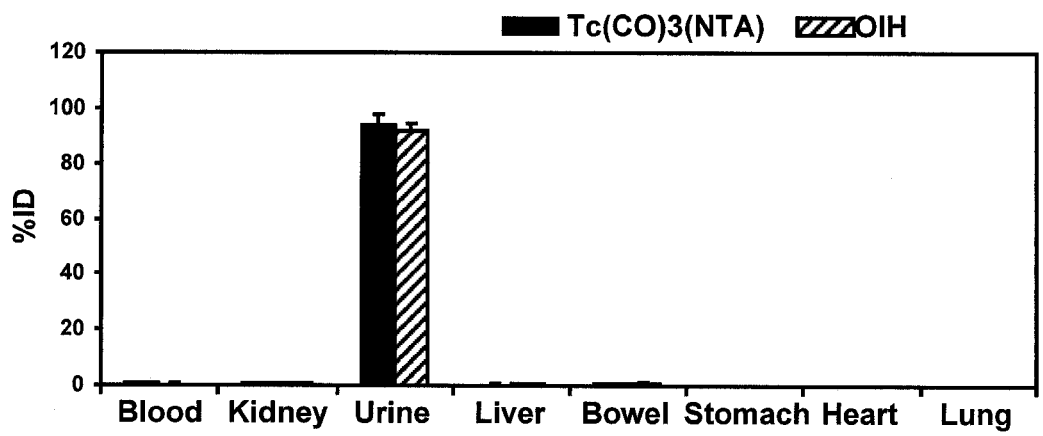
Figure 3C:
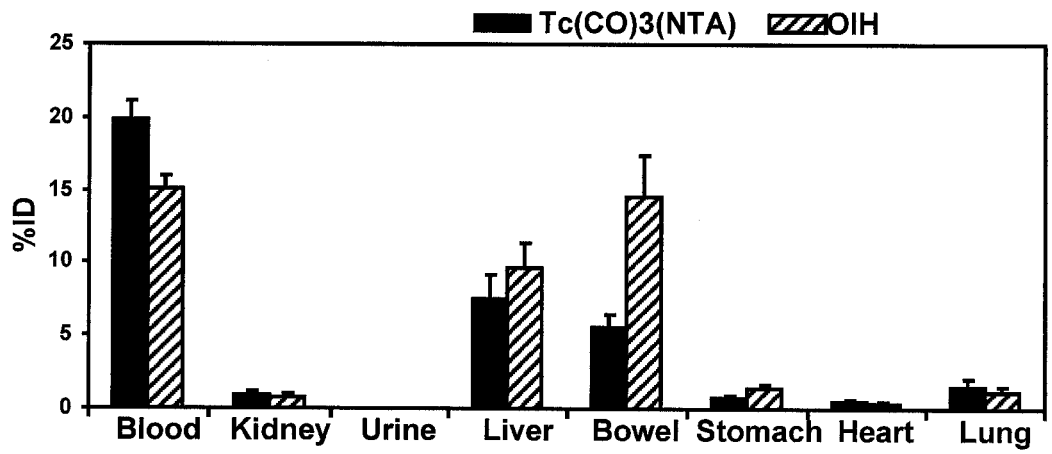

The biodistributions of $Na_2[^{99m}Tc(CO)_3(NTA)]$ in normal rats (Group A) and in rats with simulated renal failure (Group B) is shown in Table 3, below, and FIGS. 3A-3C.

Example 7

Biodistribution Studies $Na_2[^{99m}Tc(CO)_3(NTA)]$ was evaluated in two experimental groups of Sprague-Dawley rats. Rats in both groups were anesthetized with ketamine-xylazine (2 mg/kg of body weight) injected intramuscularly, with additional supplemental anesthetic as needed. In the first group of ten normal rats (Group A), the bladder was catheterized by use of heat-flared PE-50 tubing. In the second group of six rats (Group B), the abdomen was open by a midline incision and both renal pedicles were ligated to produce a model of renal failure; thus no urine was collected.

TABLE 3

Percent injected dose of $[^{99m}Tc(CO)_3(NTA)]^{2-}$ and $^{131}I$-OIH in blood, urine and selected organs at 10 and 60 Minutes in normal rats (Group A, n = 5 at each sampling time) and in rats with renal pedicle ligation (Group B, n = 6).

| | Blood | | Kidney | | Urine | | % $^{99m}Tc/$ $^{131}I$-OIH | Liver | Bowel | |
|---|---|---|---|---|---|---|---|---|---|---|
| | $^{99m}Tc$-NTA | $^{131}I$-OIH | $^{99m}Tc$-NTA | $^{131}I$-OIH | $^{99m}Tc$-NTA | $^{131}I$-OIH | | $^{131}I$-OIH | $^{99m}Tc$-NTA | $^{131}I$-OIH |
| Group A | | | | | | | | | | |
| 10 min | 4.2 ± 0.9 | 5.6 ± 1.0 | 6.1 ± 0.7 | 5.6 ± 0.6 | 57.1 ± 8.4 | 53.2 ± 7.2 | 108 ± 9 | 4.0 ± 0.7 | 0.7 ± 0.3 | 2.2 ± 0.4 |
| 60 min | 0.4 ± 0.2 | 0.5 ± 0.0 | 0.4 ± 0.2 | 0.5 ± 0.0 | 93.0 ± 4.0 | 91.4 ± 3.7 | 101 ± 5 | 0.6 ± 0.3 | 0.4 ± 0.1 | 1.0 ± 0.5 |
| Group B | | | | | | | | | | |
| 60 min | 19.9 ± 1.2 | 15.1 ± 0.9 | 0.9 ± 0.2 | 0.8 ± 0.2 | — | — | — | 9.7 ± 1.7 | 5.6 ± 0.9 | 14.6 ± 2.8 |

All results are expressed as the mean±SD. To determine the statistical significance of differences between the 2 groups, comparisons were made with the 2-tailed Student t test for paired data; P<0.05 was considered to be statistically significant.

In the normal, Group A rats the blood clearance of $Na_2[^{99m}Tc(CO)_3(NTA)]$ was rapid and comparable to $^{131}$I-OIH, with only 4.2±0.9% of the injected dose remaining in the blood 10 mins after injection, and 0.4±0.2% at 60 mins (Table 3). The activity of $Na_2[^{99m}Tc(CO)_3(NTA)]$ in urine as a percentage of $^{131}$I-OIH was 108±9% at 10 min, and 101±5% at 60 min; there was no difference in the percent injected dose in the urine for $Na_2[^{99m}Tc(CO)_3(NTA)]$ and $^{131}$I-OIH at 10 and 60 min, P=0.14 and 0.5, respectively. $Na_2[^{99m}Tc(CO)_3(NTA)]$ demonstrated a high specificity of renal excretion with less than a mean of 0.8% of the total injected activity present in heart, lungs, spleen, blood and liver at 60 min, compared to 1.1% for $^{131}$I-OIH (P=0.01).

The Group B rats had ligation of both renal pedicles to simulate renal failure. $Na_2[^{99m}Tc(CO)_3(NTA)]$ was better retained in the blood at 60 minutes (19.9%), compared with $^{131}$I-OIH (15.1%), P<0.001. Bowel activity was substantially less for $Na_2[^{99m}Tc(CO)_3(NTA)]$ than for $^{131}$I-OIH, 5.6% versus 14.6%, respectively (P<0.001), indicating that renal failure results in less hepatobiliary excretion or intestinal secretion of $Na_2[^{99m}Tc(CO)_3(NTA)]$ than $^{131}$I-OIH (Table 1). The minimal renal activity noted with both tracers was probably secondary to capsular blood flow (Table 3, FIGS. 3A-3C).

The plasma protein binding of $Na_2[^{99m}Tc(CO)_3(NTA)]$ averaged 67±7% and erythrocyte uptake was low, 7±2%, compared to 44±10% and 35±1%, respectively, for $^{131}$I-OIH. The plasma clearance of $Na_2[^{99m}Tc(CO)_3(NTA)]$ was comparable to that of $^{131}$I-OIH, 3.08 mL/min/100 g versus 2.96 mL/min/100 g, respectively. The extraction fraction of $Na_2[^{99m}Tc(CO)_3(NTA)]$ was 93.5±3.8% versus 67.9±6.1% for $^{131}$I-OIH.

Example 8

Renal Clearance, Extraction Fraction, Plasma Protein Binding and Erythrocyte Uptake Two male rats were anesthetized as described above and placed on a heated surgical table. Following tracheostomy, the left jugular vein was cannulated with two pieces of PE-50 tubing (one for infusion of radiopharmaceuticals and one to infuse normal saline (5.8 mL/h) to maintain hydration and additional anesthetic (5 mg/h) as necessary). The right carotid artery was cannulated for blood sampling and the bladder was catheterized by use of PE-50 tubing. The core temperature of each animal was continually monitored throughout the study using a rectal temperature probe. $Na_2[^{99m}Tc(CO)_3(NTA)]$ (3.7 MBq/mL [100 µCi/mL]) and $^{131}$I-OIH (1.85 MBq/mL [50 µCi/mL]), were co-infused at a flow rate of 1.7 ml/h for 60 mins to establish steady-state blood levels. Urine was then collected for three 10-min clearance periods and midpoint blood samples (0.5 mL) were obtained. The blood samples were centrifuged for 15 mins and plasma samples were obtained. Plasma clearance (Cl) was determined by utilizing the equation: Cl (mL/min)=UV/P, where U is the urine radioactivity concentration, V is the urine volume excreted per minute and P is the plasma radioactivity concentration. The average of the three 10-min clearance measurements was used as the clearance value.

The extraction fraction (EF) was measured at the conclusion of the clearance measurements by obtaining a left renal venous blood sample (0.5 mL) followed immediately by a carotid artery sample (3 mL). Both blood samples were centrifuged immediately after collection to obtain plasma samples. EF was calculated by measuring the difference between the arterial and venous plasma sample: EF=(arterial concentration−venous concentration)/arterial concentration.

Plasma protein binding (PPB) was determined by ultrafiltration (Centrifree micropartition system; Amicon Inc.) of 1 mL of plasma obtained from the carotid artery sample: PPB= [1−(ultrafiltrate concentration/plasma concentration)]×100. Arterial blood samples were placed in capillary tubes and centrifuged to determine the hematocrit. Samples of the whole blood and packed cells (about 0.3 mL each) were pipetted into counting tubes, weighed, and counted. The percent uptake in the erythrocytes was calculated from the whole blood (counts/g) and packed cells (counts/g). Percent erythrocyte uptake=[(counts/g in erythrocytes×hematocrit)/ counts/g in whole blood]. No correction was made for plasma trapped in the red blood cells sample. PPB and erythrocyte uptake were calculated in duplicate and the mean values reported.

Example 9

Figure 4:
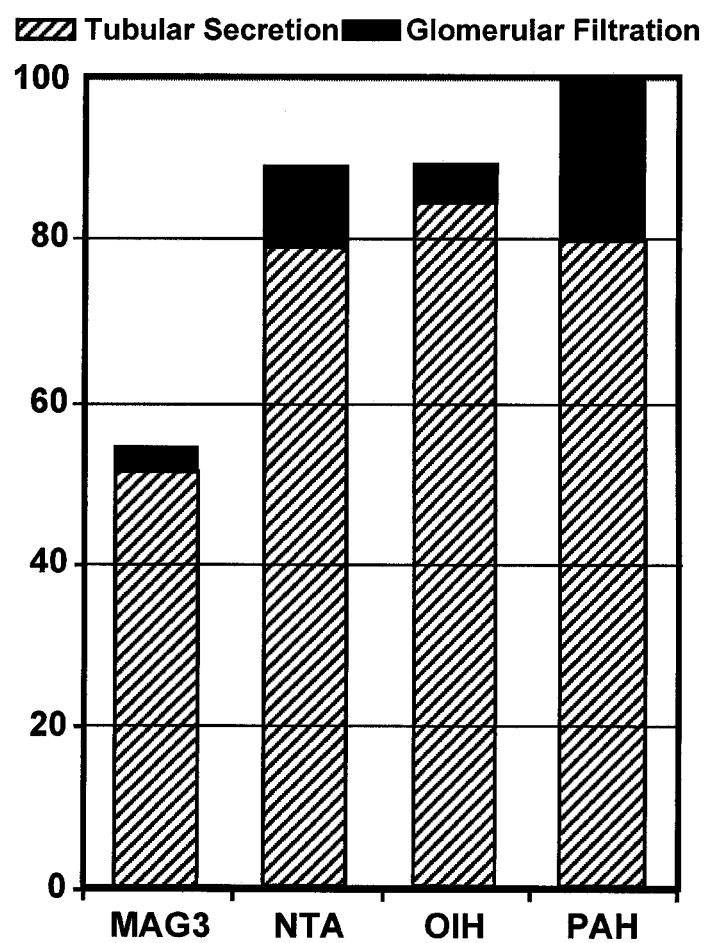
FIG. 4 illustrates a comparison of renal tracers in human subjects. In the figure, PAH is assigned a clearance of 100%; the solid area represents the percent that is removed by the kidney through glomerular filtration. The cross-hatched areas represent the percent removed by tubular secretion. OIH ($^{131}$I-OIH) and NTA ($^{99m}$Tc(CO)$_3$(NTA) have comparable clearances, about 90% that of PAH. The clearance of MAG3 ($^{99m}$Tc-MAG3) is substantially less than that of PAH.

PAH (para-aminohippuric acid) is a non-radioactive agent that is almost completely cleared with each pass through the kidneys; consequently, it provides a measure of effective renal plasma flow. The renal clearance is dependent on glomerular filtration and tubular secretion. As is shown in FIG. 4, PAH is assigned a clearance of 100%; the solid areas represents the percent that is removed by the kidney through glomerular filtration, and the hatched areas represent the percent removed by tubular secretion. $^{131}$I-OIH and the $^{99m}$Tc-(CO)$_3$ (NTA) of the present disclosure have comparable clearances, about 90% that of PAH. The clearance of $^{99m}$TcMAG3 is substantially less.

Example 10

Human Studies

Five healthy volunteers (3 male, 2 females; mean age±SD, 39.4±12.7 yrs; range 20-55 yrs) participated in this study. Inclusion criteria required the absence of any history of kidney and bladder diseases and a normal review of systems. Pregnancy was excluded in females by means of a urine pregnancy test. Measurements of blood pressure, heart rate, and temperature were taken pre- and post-injection for each volunteer; in addition a CBC, standard chemistry panel and urinalysis were obtained pre- and 24 hr post-injection of $^{99m}$Tc(CO)$_3$(NTA).

Approximately 74 MBq (about 2 mCi) of $^{99m}$Tc(CO)$_3$ (NTA) was co-injected with 7.4-11.1 MBq (200-300 µCi) of $^{131}$I-OIH, and imaging was performed by using a General Electric Infinia (Milwaukee, Wis.) camera with a ⅜ inch crystal fitted with a high energy collimator; a 20% window was centered over the 365 KeV photopeak of $^{131}$I, and a second 20% window was centered over the 140 keV photopeak of $^{99m}$Tc. Data were acquired in a 128×128 matrix by using a three-phase dynamic acquisition and processed on a General Electric Xeleris computer using QuantEM™ 2.0 renal software.

Blood samples were obtained at 3, 5, 10, 20, 30, 45, 60, and 90 mins after injection. Plasma clearances for $^{131}$I-OIH and $^{99m}$Tc(CO)$_3$(NTA) were determined using the single injection, two-compartment model of Sapirstein et al., ((1955) Am. J. Physiol. 181: 330-336, incorporated herein by reference in its entirety). The volunteers voided at 30, 90, and 180 mins post-injection to determine the percent dose in the urine at each time period. Plasma protein binding (PPB) was determined by ultracentrifugation (CENTRIFREE™ microparition system, Amicon Inc.) of 1 mL of plasma:

PPB=(1.0−[ultrafiltrate concentration/plasma concentration])×100

A Beckman gamma counter system was used to determine the concentration of radioactivity in plasma, in red blood cells and in urine samples with correction for $^{131}$I scatter into the $^{99m}$Tc window. To determine if the complex was metabolized or excreted unchanged in the urine, a 1 mL urine sample from the urine collection at 30 mins was obtained from each volunteer and analyzed by HPLC alone and with purified complex added.

There was no evidence of any toxicity based on measurements of blood pressure, heart rate, temperature, CBC, standard hematology, chemistry panel or urine analysis for any of the volunteers. The clearance of $^{99m}$Tc(CO)$_3$(NTA) averaged 480 mL/min, almost identical to the 482 mL/min clearance of $^{131}$I-OIH, as shown in Table 4.

TABLE 4

Comparison of $^{99m}$Tc(CO)$_3$(NTA) and $^{131}$I-OIH in normal volunteers (n = 5).

| Vol. | $^{99m}$Tc-NTA Cl (ml/min) | PPB (%) | RBC (%) | Urine (%) | Clear NTA/OIH | Urine NTA/OIH | $^{131}$I-OIH Clear (ml/min) | PPB (%) | RBC (%) | Urine (%) |
|---|---|---|---|---|---|---|---|---|---|---|
| 1 | 388.5 | 50 | 20 | 91 | 78% | 95% | 497.49 | 79 | 25 | 96 |
| 2 | 434.2 | 42 | 16 | 88 | 98% | 106% | 442 | 74 | 24 | 83 |
| 3 | 491.8 | 53 | 4 | 84 | 80% | 104% | 613.4 | 79 | 14 | 81 |
| 4 | 477.1 | 39 | 6 | 88 | 113% | 90% | 423.4 | 74 | 15 | 98 |
| 5 | 607.9 | 40 | 15 | 82 | 140% | 88% | 433.4 | 79 | 21 | 93 |
| mean | 479.90 | 45 | 12 | 87 | 102% | 99% | 481.94 | 77 | 20 | 90 |
| (SD) | 82.12 | 6.30 | 6.87 | 3.58 | 25.7% | 8.1% | 78.90 | 2.74 | 5.07 | 7.73 |

The plasma protein binding was 45% for $^{99m}$Tc(CO)$_3$(NTA) compared to 77% for $^{131}$I-OIH. Red cell uptake was 12% for $^{99m}$Tc(CO)$_3$(NTA) compared to 20% for $^{131}$I-OIH. $^{99m}$Tc(CO)$_3$(NTA) was excreted as rapidly as $^{131}$I-OIH; the ratio of $^{99m}$Tc(CO)$_3$(NTA)/$^{131}$I-OIH in the urine at 30 minutes was 97%, as shown in Table 5.

TABLE 5

Comparison of the rate of excretion of $^{99m}$Tc(CO)$_3$(NTA) and $^{131}$I-OIH at 30 minutes in normal volunteers

| VOL. | Urine 30 min $^{99m}$Tc(CO)$_3$(NTA) | Urine 30 min $^{131}$I-OIH | Urine 30 min $^{99m}$Tc/$^{131}$I |
|---|---|---|---|
| 1 | 73% | 78% | 94% |
| 2 | 58% | 55% | 105% |
| 3 | 67% | 64% | 105% |
| 4 | 73% | 80% | 91% |
| 5 | 67% | 74% | 91% |
| mean | 67.60% | 70.20% | 97.10% |
| (SD) | 6.15% | 10.50% | 7.36% |

Figure 5:
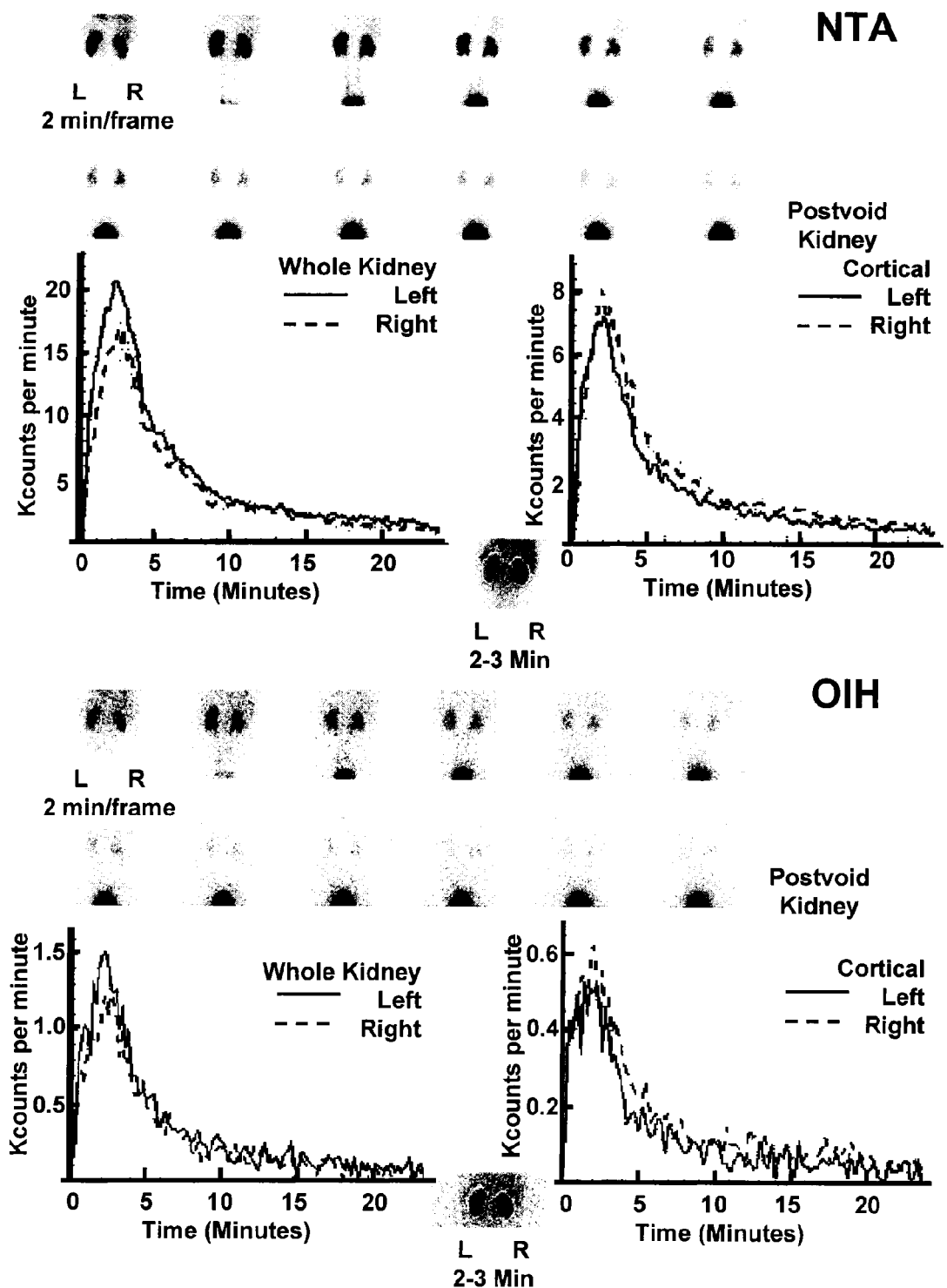
FIG. 5 illustrates a comparison between renogram curves and 2-min $^{99m}$Tc(CO)$_3$(NTA) images and simultaneously acquired $^{131}$I-OIH renogram curves and 2-min images. The renogram curves using $^{99m}Tc(CO)_3(NTA)$ appear identical to those of the gold standard, $^{131}I$-OIH, and the image quality is better.

Image quality was excellent with $^{99m}$Tc(CO)$_3$(NTA) with the renogram curves having an appearance almost identical to that of $^{131}$I-OIH (FIG. 5). Representative $^{99m}$Tc(CO)$_3$(NTA) images and renogram curves, as well as simultaneous $^{131}$I-OIH images and curves are shown in FIG. 5.

REFERENCES

Alberto R, Schibli R, Egli A, Schubiger A P. A Novel organometallic aqua complex of technetium for the labeling of biomolecules: Synthesis of [$^{99m}$Tc(OH$_2$)$_3$(CO)$_3$]$^+$ from [$^{99m}$TcO$_4$]$^-$ in aqueous solution and its reaction with a bifunctional ligand. J Am Chem. Soc. 1998; 120:7987-7988.

Alberto R, Ortner K, Wheatley N, Schibli R, Schubiger A P. Synthesis and properties of boranocarbonate: A convenient in situ CO source for the aqueous preparation of [$^{99m}$Tc(OH$_2$)$_3$(CO)$_3$]$^+$. J Am Chem. Soc. 2001; 123:3135-3136.

Hansen L, Marzilli L G, Eshima D, Malveaux E, Folks R, Taylor A. Evaluation of technetium-99m-triamide-mercaptide complexes designed to identify properties favoring renal tubular transport. J Nucl Med. 1994; 35:1198-1205.

Hansen L, Lipowska M, Melendez E, et al. Factors influencing the pK$_a$ of ligated amines and the syn/anti isomerization in cysteine-based Re(V)═O(N$_2$S$_2$) radiopharmaceutical analogues as revealed by a vovel dominant tautomer in the solid. Inorg Chem. 1999; 38:5351-5358.

Hermann H J, Lange D, Eisenhut M, Schenck P, zum Winkel K. Radiation dose and labeling of hippuran. Contr Nephrol. 1978; 11:100-104.

Hosick T A, Watts F C, Meschan I. The removal and control of iodide-131 contamination in sodium o-$^{131}$I hippurate. J Nucl Med. 1966; 7:643-646.

Rattat D, Verbruggen A, Schmalle H, Berkeb H, Alberto R. [M(CO)$_2$(NO)]$^{2+}$, a new core in bioorganometallic chemistry: model complexes of [Re(CO)$_2$(NO)]$^{2+}$ and [$^{99m}$Tc(CO)$_2$(NO)]$^{2+}$. Tetrahedron Lett. 2004; 45:4089-4092.

Schibli R, Schubiger P A. Current use and future potential of organometallic radiopharmaceuticals. Eur J Nucl Med. 2002; 29:1529-1542.

Taylor A, Eshima D, Fritzberg A R, Christian P E, Kasina S. Comparison of iodine-131 OIH and technetium-99m MAG3 renal imaging in volunteers. J Nucl Med. 1986; 27:795-803.

Taylor A T, Lipowska M, Hansen L, Malveaux E, Marzilli L G. $^{99m}$Tc-MAEC complexes: new renal radiopharmaceuticals combining characteristics of $^{99m}$Tc-MAG3 and $^{99m}$Tc-EC. J Nucl Med. 2004; 45:885-891.

We claim:

1. A method of imaging a kidney in an animal or human subject, the method comprising:
   (a) administering to an animal or human subject an amount of a renal tracer, wherein the renal tracer comprises technetium-99m tricarbonyl-nitrilotriacetic acid ($^{99m}$Tc(CO)$_3$(NTA));
   (b) detecting $^{99m}$Tc(CO)$_3$(NTA) in the kidney of the animal or human subject with a gamma camera; and
   (c) obtaining at least one image of the kidney of the animal or human subject, wherein the image is obtained as a data output from a gamma camera.

2. The method of claim 1, further comprising periodically repeating the steps (a)-(c), thereby providing a time-dependent analysis of the urinary tract function of an animal or human subject, wherein the analysis is selected from the group consisting of: the EPRF of a kidney, the ability of a kidney to extract the tracer from the blood, the ability of the subject human or animal to excrete the tracer into the collecting system of a kidney, the monitoring of drainage of the tracer from the collecting system (calyces and pelvis) to the bladder, and the quantification of the ability of the bladder to empty.

3. The method of claim 2, wherein the steps (a)-(c) are repeated at time intervals over a period of about 2 min to 60 mins, thereby providing a time-dependent series of images.

4. The method of claim 2, wherein the steps (a)-(c) are repeated at time intervals over a period of about 3 min to 60 mins, thereby providing a time-dependent series of images.

5. A method of measuring effective renal plasma flow in an animal or human subject, the method comprising:
- (a) administering to an animal or human subject an amount of a renal tracer, wherein the renal tracer comprises $^{99m}Tc(CO)_3(NTA)$;
- (c) obtaining at least one image of a kidney of the animal or human subject, wherein the image is obtained as a data output from a gamma camera; and
- (d) analyzing the data output from the gamma camera, wherein the data analysis provides a measurement of the effective renal plasma flow of the animal or human subject.

6. A method of measuring effective renal plasma flow in an animal or human subject, comprising:
- administering to an animal or human subject a dose amount of a composition, wherein the composition comprises the renal tracer $^{99m}Tc(CO)_3(NTA)$;
- isolating a plurality of biological samples from the animal or human subject after administering the renal tracer;
- quantitatively measuring the amount of the renal tracer in the isolated biological samples; and
- determining the effective renal plasma flow of the animal or human subject.

7. The method of claim 6, wherein the biological sample is a plasma sample.

8. A kit comprising: an amount of the tracer $^{99m}Tc(CO)_3(NTA)$ in a sealed container, wherein the amount of the tracer is suitable for imaging a kidney of an animal or human subject, and instructions for the use thereof in imaging said kidney, the instructions comprising the steps of:
- administering to an animal or human subject an amount of a renal tracer, wherein the renal tracer comprise the renal tracer technetium-99m tricarbonyl-nitrilotriacetic acid ($^{99m}Tc(CO)_3(NTA)$);
- detecting $^{99m}Tc(CO)_3(NTA)$ in the kidney of the animal or human subject with a gamma camera; and
- obtaining at least one image of the kidney of the animal or human subject, wherein the image is obtained as a data output from a gamma camera.

9. The kit according to claim 8, wherein the instructions further comprise steps for the use of the tracer in measuring renal function, the instructions further comprising the step of:
- administering to an animal or human subject an amount of a renal tracer, wherein the renal tracer comprises $^{99m}Tc(CO)_3(NTA)$;
- obtaining at least one image of a kidney of the animal or human subject, wherein the image is obtained as a data output from a gamma camera; and
- analyzing the data output from the gamma camera, wherein the data analysis provides a measurement of the effective renal plasma flow of the animal or human subject.

10. The kit according to claim 8, wherein the instructions further comprise the steps for the use of the tracer in measuring renal function, the instructions further comprising the steps of:
- administering to an animal or human subject an amount of a renal tracer, wherein the renal tracer comprises $^{99m}Tc(CO)_3(NTA)$;
- isolating a plurality of biological samples from the animal or human subject after administering the renal tracer;
- quantitatively measuring the amount of the renal tracer in the isolated biological samples; and
- determining the effective renal plasma flow of the animal or human subject.

\* \* \* \* \*